United States Patent
Libbus et al.

(10) Patent No.: US 9,357,932 B2
(45) Date of Patent: Jun. 7, 2016

(54) SYSTEM AND METHODS FOR WIRELESS BODY FLUID MONITORING

(71) Applicant: Medtronic Monitoring, Inc., San Jose, CA (US)

(72) Inventors: Imad Libbus, St. Paul, MN (US); Mark J. Bly, Falcon Heights, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 0 days.

(21) Appl. No.: 14/720,160

(22) Filed: May 22, 2015

(65) Prior Publication Data

US 2015/0250405 A1 Sep. 10, 2015

Related U.S. Application Data

(63) Continuation of application No. 13/751,858, filed on Jan. 28, 2013, now abandoned, which is a continuation of application No. 12/210,078, filed on Sep. 12, 2008, now Pat. No. 8,374,688.

(60) Provisional application No. 61/055,666, filed on May 23, 2008, provisional application No. 60/972,512, filed on Sep. 14, 2007, provisional application No. 60/972,537, filed on Sep. 14, 2007.

(51) Int. Cl.
*A61B 5/02* (2006.01)
*G06F 19/00* (2011.01)
(Continued)

(52) U.S. Cl.
CPC .......... *A61B 5/02028* (2013.01); *A61B 5/0004* (2013.01); *A61B 5/0006* (2013.01); *A61B 5/0008* (2013.01); *A61B 5/02055* (2013.01); *A61B 5/02405* (2013.01); *A61B 5/044* (2013.01); *A61B 5/04012* (2013.01); *A61B 5/0452* (2013.01); *A61B 5/04085* (2013.01); *A61B 5/04087* (2013.01); *A61B 5/0531* (2013.01); *A61B 5/0535* (2013.01);
(Continued)

(58) Field of Classification Search
CPC .......... A61B 5/02055; A61B 5/04085; A61B 5/0452; A61B 5/0537; A61B 5/6833; A61B 5/04087; A61B 5/3431; A61B 5/7275; A61B 5/0535; A61B 5/4875; A61B 5/044; A61B 5/04012; A61B 5/02028; A61B 5/0008; A61B 5/746; A61B 5/7264; A61B 5/1118; A61B 5/1116; A61B 5/1114; A61B 5/0006; A61B 5/0004; A61B 5/7282; A61B 5/443; A61B 5/0531; A61B 5/02405; A61B 5/0816; A61B 5/0002; A61B 5/0245; A61B 5/01; A61B 5/08; A61B 5/6885; A61B 2562/0209; A61B 2562/043; A61B 2560/0412; G06F 19/3418
USPC .................. 600/306, 372, 382, 393, 547, 554
See application file for complete search history.

(56) References Cited

U.S. PATENT DOCUMENTS 5,836,942 A * 11/1998 Netherly et al. ................ 606/32
2008/0275465 A1 * 11/2008 Paul et al. ..................... 606/129
2008/0281319 A1 * 11/2008 Paul et al. ....................... 606/41

*Primary Examiner* — Rene Towa
(74) *Attorney, Agent, or Firm* — Billion & Armitage; Michael A. Collins

(57) ABSTRACT

An adherent device to monitor a tissue hydration of a patient comprises an adhesive patch to adhere to a skin of the patient. A plurality of electrodes are connected to the patch and capable of electrically coupling to the patient. Circuitry is coupled to the plurality of electrodes to measure a tissue resistance of the patient at a first frequency and to detect a low frequency droop in the measured tissue resistance. In response to detected low frequency droop, the circuitry is configured to measure a tissue resistance of the patient at a second frequency that is lower than the first frequency to verify the detection of low frequency droop, and to temporarily suspend data collection based on the detection and verification of low frequency droop.

16 Claims, 20 Drawing Sheets

(51) Int. Cl.

| | |
|---|---|
| *A61B 5/0205* | (2006.01) |
| *A61B 5/024* | (2006.01) |
| *A61B 5/0408* | (2006.01) |
| *A61B 5/0452* | (2006.01) |
| *A61B 5/053* | (2006.01) |
| *A61B 5/00* | (2006.01) |
| *A61B 5/04* | (2006.01) |
| *A61B 5/044* | (2006.01) |
| *A61B 5/11* | (2006.01) |
| *A61B 5/08* | (2006.01) |
| *A61B 5/01* | (2006.01) |
| *A61B 5/0245* | (2006.01) |

(52) U.S. Cl.
CPC ............. *A61B5/0537* (2013.01); *A61B 5/1114* (2013.01); *A61B 5/1116* (2013.01); *A61B 5/1118* (2013.01); *A61B 5/443* (2013.01); *A61B 5/4875* (2013.01); *A61B 5/6833* (2013.01); *A61B 5/7264* (2013.01); *A61B 5/7275* (2013.01); *A61B 5/7282* (2013.01); *A61B 5/746* (2013.01); *G06F 19/3418* (2013.01); *G06F 19/3431* (2013.01); *A61B 5/0002* (2013.01); *A61B 5/01* (2013.01); *A61B 5/0245* (2013.01); *A61B 5/08* (2013.01); *A61B 5/0816* (2013.01); *A61B 5/6885* (2013.01); *A61B 2560/0412* (2013.01); *A61B 2560/0468* (2013.01); *A61B 2562/0209* (2013.01); *A61B 2562/0214* (2013.01); *A61B 2562/043* (2013.01); *A61B 2562/164* (2013.01)

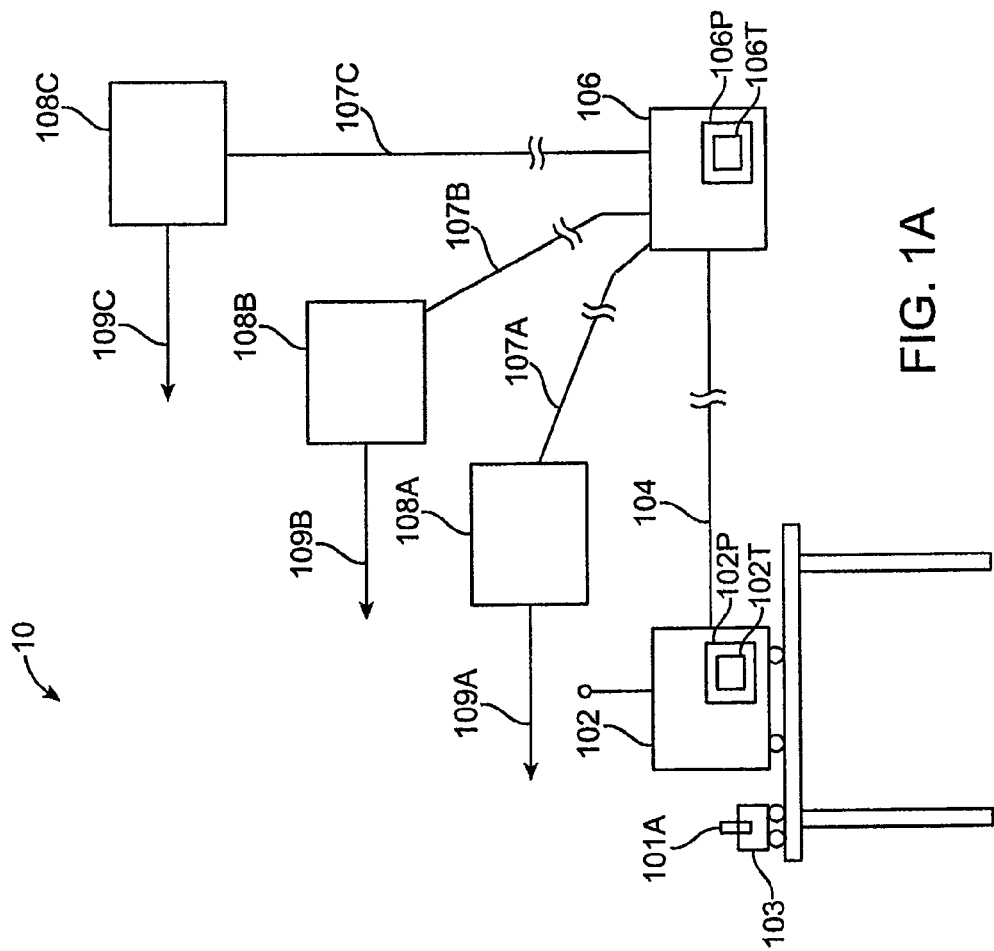
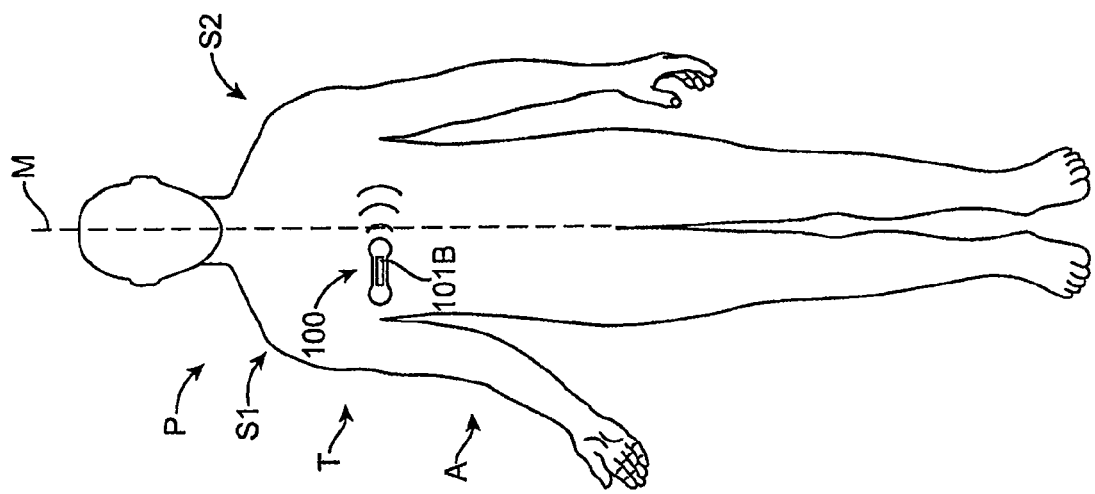
FIG. 1A

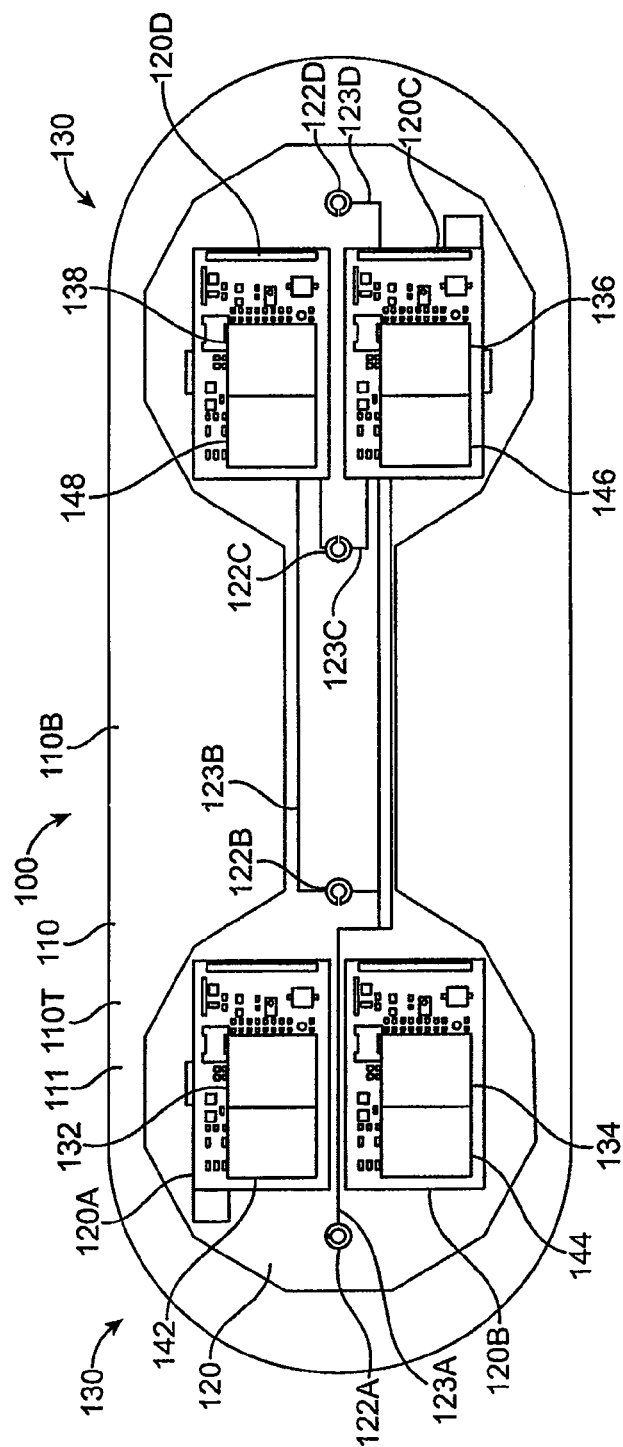
FIG. 1D
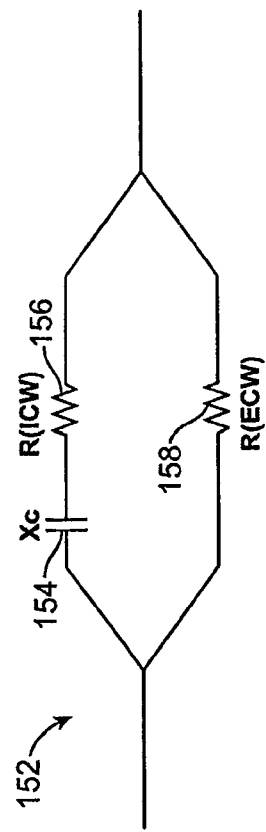
FIG. 1D1

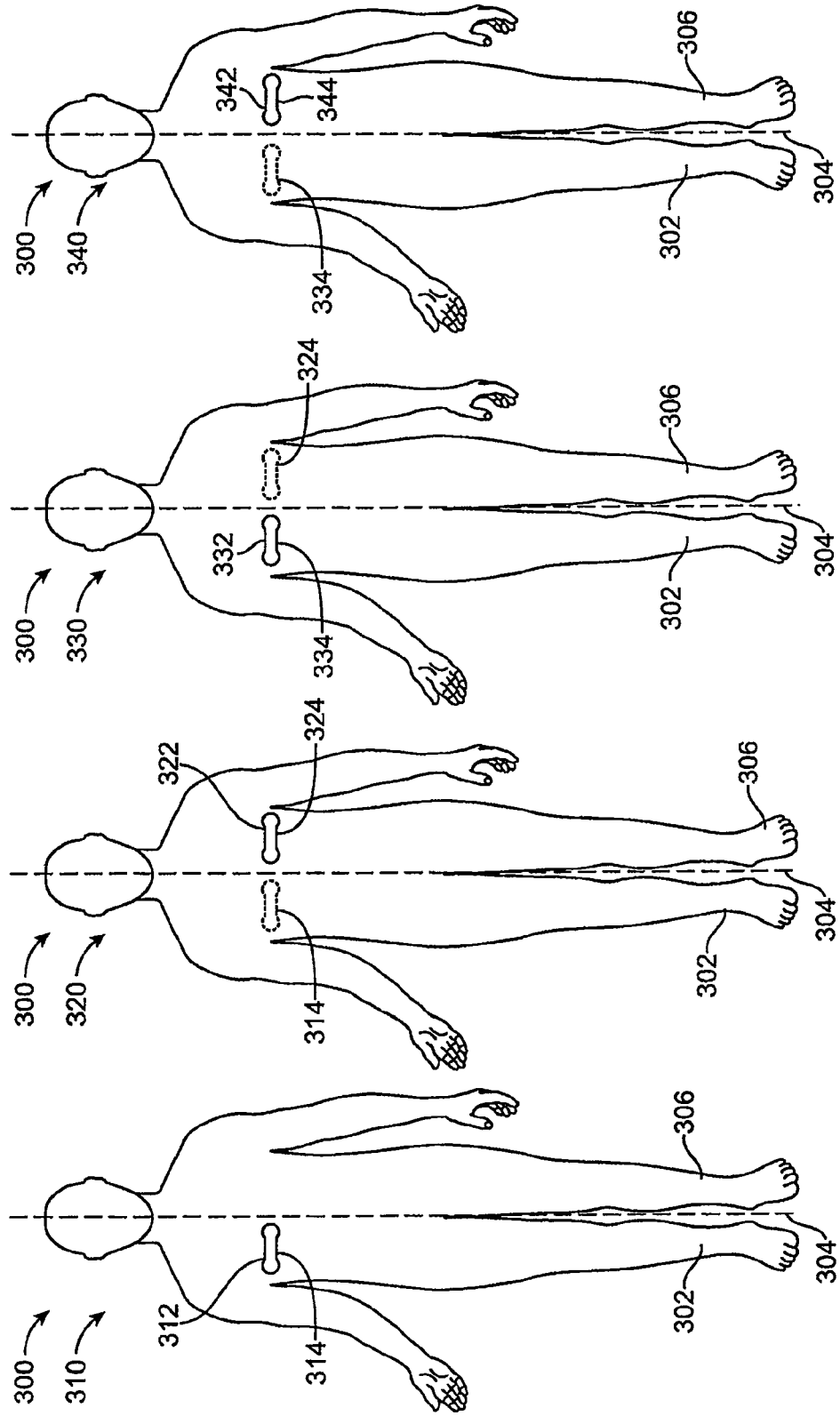

SYSTEM AND METHODS FOR WIRELESS BODY FLUID MONITORING

CROSS-REFERENCES TO RELATED APPLICATIONS

This application is a Continuation of U.S. application Ser. No. 13/751,858, filed on 28 Jan. 2013, which is a Continuation of U.S. application Ser. No. 12/210,078, filed on 12 Sep. 2008, which claims benefit of U.S. Provisional Application No. 61/055,666, filed on 23 May 2008, and also of U.S. Provisional Application No. 60/972,512, filed on 14 Sep. 2007, and also of U.S. Provisional Application No. 60/972,537, filed on 14 Sep. 2007, and which applications are all incorporated herein by reference. A claim of priority to all, to the extent appropriate, is made.

The subject matter of the present application is related to the following applications: 60/972,329; 60/972,354; 60/972,616; 60/972,363; 60/972,343; 60/972,581; 60/972,629; 60/972,316; 60/972,333; 60/972,359; 60/972,336; and 60/972,340 all of which were filed on Sep. 14, 2007; 61/046,196 filed Apr. 18, 2008; 61/047,875 filed Apr. 25, 2008; 61/055,645, 61/055,656, and 61/055,662 all filed May 23, 2008; and 61/079,746 filed Jul. 10, 2008.

BACKGROUND OF THE INVENTION

1. Field of the Invention

The present invention relates to patient monitoring. Although embodiments make specific reference to monitoring impedance and electrocardiogram signals with an adherent patch, the system methods and device described herein may be applicable to many applications in which physiological monitoring is used, for example wireless physiological monitoring for extended periods.

Patients are often treated for diseases and/or conditions associated with a compromised status of the patient, for example a compromised physiologic status. In some instances, a patient may report symptoms that require diagnosis to determine the underlying cause. For example, a patient may report fainting or dizziness that requires diagnosis, in which long term monitoring of the patient can provide useful information as to the physiologic status of the patient. In some instances a patient may have suffered a heart attack and require care and/or monitoring after release from the hospital. One example of a device to provide long term monitoring of a patient is the Holter monitor, or ambulatory electrocardiography device.

In addition to measuring heart signals with electrocardiograms, known physiologic measurements include impedance measurements. For example, transthoracic impedance measurements can be used to measure hydration and respiration. Although transthoracic measurements can be useful, such measurements may use electrodes that are positioned across the midline of the patient, and may be somewhat uncomfortable and/or cumbersome for the patient to wear.

Work in relation to embodiments of the present invention suggests that known methods and apparatus for long term monitoring of patients, for example in-home monitoring, may be less than ideal. At least some of the known devices may not collect the right kinds of data to treat patients optimally. For example, although successful at detecting and storing electrocardiogram signals, devices such as the Holter monitor can be somewhat bulky and may not collect all of the kinds of data that would be ideal to diagnose and/or treat a patient. In at least some instances, devices that are worn by the patient may be somewhat larger than ideal and may be uncomfortable, which may lead to patients not wearing the devices and not complying with directions from the health care provider, such that data collected may be less than ideal. Further, in at least some instances the current devices may have less than ideal performance when the patient resumes a normal lifestyle and the device is exposed to environmental factors such as humidity or water, for example, when the patient takes a shower. Although implantable devices may be used in some instances, many of these devices can be invasive and/or costly, and may suffer at least some of the shortcomings of known wearable devices.

Current methodologies for measuring patient hydration with impedance may be less than ideal for remote patient monitoring, such as in-home monitoring for extended periods. At least some of the current devices that determine hydration with impedance, for example for hospital use, may use more current and may have more complex and bulky circuitry than would be ideal for in-home monitoring in at least some instances, for example where the patient is active and moves about the home. As noted above, the size and comfort of a remote patient monitor can affect the quality of the data received from the patient.

Therefore, a need exists for improved patient monitoring, for example improved in-home patient monitoring. Ideally, such improved patient monitoring would avoid at least some of the short-comings of the present methods and devices.

2. Description of the Background Art

The following patents and publications may describe background art relevant to the present application: U.S. Pat. No. 7,133,716 to Kraemer et al.; U.S. Pat. No. 6,906,530 to Geisel; U.S. Pat. No. 6,442,422 to Duckert; U.S. Pat. No. 6,050,267 to Nardella et al.; U.S. Pat. No. 5,935,079 to Swanson et al.; U.S. Pat. No. 5,836,990 to Li; U.S. Pat. No. 5,788,643 to Feldman; U.S. Pat. No. 5,738,107 to Martinsen et al.; U.S. Pat. No. 5,449,000 to Libke et al.; U.S. Pat. No. 4,966,158 to Honma et al.; U.S. Pat. No. 4,692,685 to Blaze; U.S. Patent App. Pub. No. 2007/0043301 to Martinsen et al.; U.S. Patent App. Pub. No. 2006/0281981 to Jang et al.; U.S. Patent App. Pub. No. 2006/0004300 to Kennedy; U.S. Patent App. Pub. No. 2005/0203435 to Nakada; and U.S. Patent App. Pub. No. 2005/0192488 to Bryenton et al.

BRIEF SUMMARY OF THE INVENTION

The present invention relates to patient monitoring. Although embodiments make specific reference to monitoring impedance and electrocardiogram signals with an adherent patch, the system methods and device described herein may be applicable to any application in which physiological monitoring is used, for example wireless physiological monitoring for extended periods. Embodiments of the present invention use tissue resistance to determine patient hydration, such that the size, complexity and power consumption of the associated circuitry can be minimized. In many embodiments, tissue resistance alone is measured at a single frequency to determine patient hydration, such that the circuitry and battery size and power consumption of the device can be further minimized. In other embodiments, tissue resistance and tissue reactance are measured at a single frequency. In some embodiments, the quality of the coupling of the electrode to tissue can be determined, and such that the integrity of the measured patient data can be verified. The quality of the coupling of the electrodes to tissue can be quantified in many ways, for example with at least one of tissue resistance measured at an additional frequency, tissue reactance measured at the same frequency as the resistance, tissue impedance measured between any two electrodes, or a signal to noise ratio from electrocardiogram measurements. In many embodiments, the adherent device can be continuously worn by the patient for an extended period, for example at least one week, and reliable measurements obtained with the improved comfort and small size of the device.

In a first aspect, embodiments of the present invention provide an adherent device for heart failure patient monitoring. The device comprises an adhesive patch and at least two electrodes connected to the patch that are capable of electrically coupling to the skin of a patient. Circuitry coupled to the at least two electrodes measures a hydration signal of the patient. The hydration signal comprises bioimpedance data, for example tissue resistance, which is used to determine changes in patient body fluid. The device may use low measurement frequencies to minimize the capacitative effects and isolate the extracellular impedance. This can be beneficial for the detection of some patient conditions, for example heart failure decompensation, because the intracellular fluid does not change significantly over short periods of time, and the edema in heart failure may comprise extracellular edema.

In some embodiments, a single measurement frequency is used.

In some embodiments, multiple measurement frequencies are used to observe frequency dependent changes in the measured resistance. These observations may be used to determine the quality of the measurements taken or of the skin-electrode interface.

In some embodiments, the measured hydration signal comprises only tissue resistance.

In some embodiments, the measured hydration signal comprises tissue resistance and tissue reactance.

In another aspect, embodiments of the present invention provide a method of monitoring a patient for heart failure. An adhesive patch is adhered to a skin of the patient so as to couple at least two electrodes to the skin of the patient. Circuitry coupled to the at least two electrodes measures bioimpedance to determine changes in patient body fluid.

In another aspect, embodiments of the present invention provide an adherent device to monitor a tissue hydration of a patient. The device includes an adhesive patch that adheres to the skin of the patient and at least four electrodes connected to the patch and capable of electrically coupling to the patient. Circuitry is coupled to the at least four electrodes to measure a tissue resistance of the patient and is configured to determine the tissue hydration in response to the tissue resistance.

In some embodiments, the circuitry includes a processor system that is configured to determine the hydration of the patient in response to the tissue resistance.

In some embodiments, the impedance circuitry is configured to measure the tissue resistance at a single frequency without tissue reactance. The processor system is configured to determine the tissue hydration in response to the tissue resistance measured at the single frequency.

In some embodiments, the tissue resistance corresponds to a change in patient body fluid. A processor may be coupled to the impedance circuitry, such that the processor is configured to determine an amount of extracellular edema from the change in patient body fluid.

In some embodiments, the hydration signal of the patient comprises a measurement of extracellular fluid.

In some embodiments, the impedance circuitry is configured to measure the hydration signal using at least one low measurement frequency. The at least one low measurement frequency may be in the range of 5 to 15 kHz. The at least one low measurement frequency may comprise a single measurement frequency, which may be in the range of 0 to 10 kHz.

In other embodiments the at least one low measurement frequency may comprise multiple measurement frequencies. The hydration signal may comprise a tissue reactance measurement.

In another aspect, embodiments of the present invention provide an adherent device to monitor a patient. The device includes an adhesive patch to adhere to a skin of the patient and at least four electrodes connected to the patch and capable of electrically coupling to the patient at a skin-electrode interface. Impedance circuitry is coupled to the at least four electrodes to measure a hydration signal of the patient. The impedance circuitry is configured to measure multiple frequencies.

In some embodiments, the hydration signal comprises a tissue resistance measurement and a tissue reactance measurement.

In some embodiments, the device includes a processor coupled to the impedance circuitry, where the processor is configured to determine a quality of the skin-electrode interface from at least one of an ECG signal-to-noise ratio, a tissue reactance, tissue impedance measured between any two electrodes, or a second measurement frequency. The processor may be configured to determine the quality of the skin-electrode interface from a second measurement frequency and may be configured to measure a droop in the tissue resistance.

In another aspect, embodiments of the present invention provide a method of monitoring a patient. The method includes adhering an adhesive patch to a skin of the patient to couple at least four electrodes to the skin of the patient to form a skin-electrode interface and measuring a hydration signal of the patient with impedance circuitry that is coupled to the at least four electrodes. The hydration signal comprises a tissue resistance measurement.

In some embodiments, the tissue resistance measurement corresponds to a change in patient body fluid. The method may also include determining an amount of extracellular edema from the change in patient body fluid with a processor coupled to the impedance circuitry.

In some embodiments, the hydration signal is measured with at least one low measurement frequency. The at least one low measurement frequency may be between 0 and 10 kHz. The at least one low measurement frequency may comprise a single measurement frequency or multiple measurement frequencies.

In some embodiments, the hydration signal also includes a tissue reactance measurement. The method may also include determining a quality of the skin-electrode coupling from the tissue reactance measurement. The quality of the skin-electrode coupling may be determined by at least one of determining an ECG signal-to-noise ratio, determining a tissue reactance, measuring a tissue impedance between any two electrodes, or measuring resistance at a second measurement frequency.

In another aspect, embodiments of the present invention provide a method of monitoring a patient, where the method includes adhering an adhesive patch to the skin of the patient to couple at least four electrodes to the skin of the patient to form a skin-electrode interface. A hydration signal of the patient is measured with impedance circuitry coupled to the at least four electrodes, where the hydration signal comprises a tissue resistance measurement and a tissue reactance measurement. An amount of extracellular edema is determined from the tissue resistance measurement and a quality of skin-electrode coupling is determined from the tissue reactance measurement.

In some embodiments, the method also includes indicating a replacement status of the adhesive patch based on the quality of the skin-electrode coupling.

In another aspect, embodiments of the present invention provide an adherent device to monitor a patient. The device includes an adhesive patch to adhere to a skin of the patient and at least four electrodes mechanically coupled to the patch and capable of electrically coupling to the patient. The at least four electrodes comprise at least two force electrodes and at least two sense electrodes. Impedance circuitry is electrically coupled to the at least two force electrodes to force an electrical current and is coupled to the at least two sense electrodes to measure a hydration signal of the patient, where the hydration signal comprises a tissue resistance measurement. A processor system is coupled to the impedance circuitry and configured to determine an amount of extracellular edema from the hydration signal.

In some embodiments, the processor system is configured to calculate and report a patient risk of an adverse cardiac event to at least one of a remote center or a physician based on the amount of extracellular edema.

In another aspect, embodiments of the present invention provide a method of monitoring a patient. The method includes adhering an adhesive patch to the skin of the patient so as to couple at least four electrodes to the skin of the patient. The at least four electrodes comprise at least two force electrodes and at least two sense electrodes. A tissue resistance of the patient is measured with impedance circuitry electrically coupled to the at least two force electrodes and to the at least two sense electrodes, such that the force electrodes force an electrical current between the at least two force electrodes, wherein the impedance circuitry generates a hydration signal. An amount of extracellular edema is determined from the hydration signal.

In some embodiments, the electrical current is a low frequency current. The low frequency current may have a frequency from 0 to 10 kHz.

In some embodiments, the electrical current has a single measurement frequency.

BRIEF DESCRIPTION OF THE DRAWINGS

FIG. 1A shows a patient and a monitoring system comprising an adherent device, according to embodiments of the present invention;

FIG. 1D shows a printed circuit boards and electronic components over the adherent patch, as in FIG. 1C;

FIG. 1D-1 shows an equivalent circuit that can be used to determine optimal frequencies for determining patient hydration, according to embodiments of the present invention;

FIGS. 3A to 3D show a method of monitoring a patient for an extended period with an adherent patch with adherent patches alternatively adhered to the right side or the left side of the patient;

DETAILED DESCRIPTION OF THE INVENTION

Figure 1B:
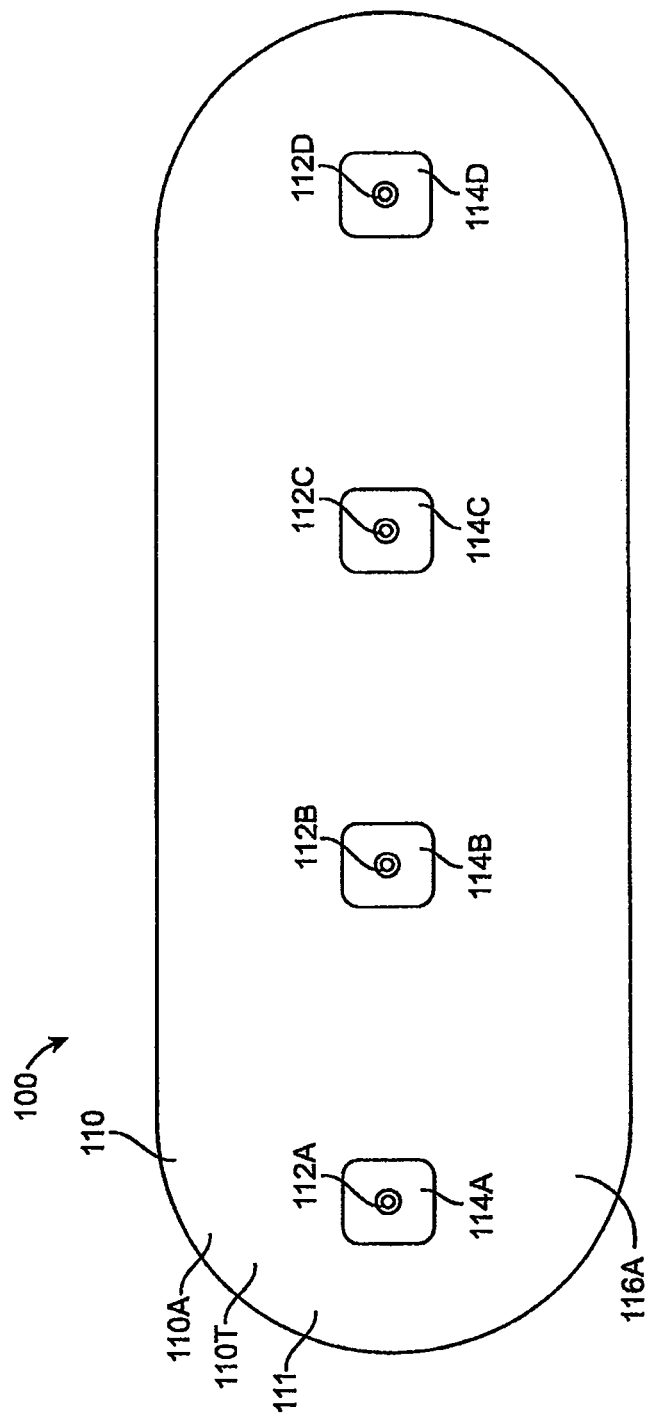
FIG. 1B shows a bottom view of the adherent device as in FIG. 1A comprising an adherent patch.

Embodiments of the present invention relate to patient monitoring. Although embodiments make specific reference to monitoring impedance and electrocardiogram signals with an adherent patch, the system methods and device described herein may be applicable to any application in which physiological monitoring is used, for example wireless physiological monitoring for extended periods.

Decompensation is failure of the heart to maintain adequate blood circulation. Although the heart can maintain at least some pumping of blood, the quantity is inadequate to maintain healthy tissues. Several symptoms can result from decompensation including pulmonary congestion, breathlessness, faintness, cardiac palpitation, edema of the extremities, and enlargement of the liver. Cardiac decompensation can result in slow or sudden death. Sudden Cardiac Arrest (hereinafter "SCA"), also referred to as sudden cardiac death, is an abrupt loss of cardiac pumping function that can be caused by a ventricular arrhythmia, for example ventricular tachycardia and/or ventricular fibrillation. Although decompensation and SCA can be related in that patients with decompensation are also at an increased risk for SCA, decompensation is primarily a mechanical dysfunction caused by inadequate blood flow, and SCA is primarily an electrical dysfunction caused by inadequate and/or inappropriate electrical signals of the heart.

Embodiments may use bioimpedance to measure changes in patient body fluid to aid in heart failure patient monitoring, for example changes in resistance to detect an impending decompensation. Because intracellular fluid does not change significantly over short periods of time, and edema in heart failure comprises extracellular edema, the device can use low measurement frequencies, for example 0-10 kHz, to minimize capacitive effects and isolate extracellular impedance.

Although some embodiments may use a single measurement frequency, multiple measurement frequencies may also be used. Frequency-dependent changes in measured resistance may be used to determine the quality of the measurement and of the skin-electrode interface, such as with adherent and/or wearable embodiments. For example, wetting during showering can cause a low frequency droop in measured resistance, which may indicate that data collection should be temporarily suspended.

Bioimpedance comprises two components, tissue resistance and tissue reactance, and change in body fluid can be closely correlated with change in the tissue resistance. In many embodiments, tissue resistance is measured and tracked, such that it may not be necessary to measure the reactance. For example, relative body fluid change can be determined in a computationally efficient manner in response to the measured resistance, such that the relative change in body fluid can be determined without measurement of reactance and without a determination of absolute body fluid.

Although the quality of the skin electrode interface can be determined in many ways, in many embodiments, tissue reactance may be used to measure the quality of the skin-electrode coupling. For example, resistance may be used to track changes in body fluid, and reactance used to determine the quality of the skin-electrode interface. An increase in reactance may indicate a degradation of skin-electrode contact, and can be used as a replacement indicator.

Figure 6A:
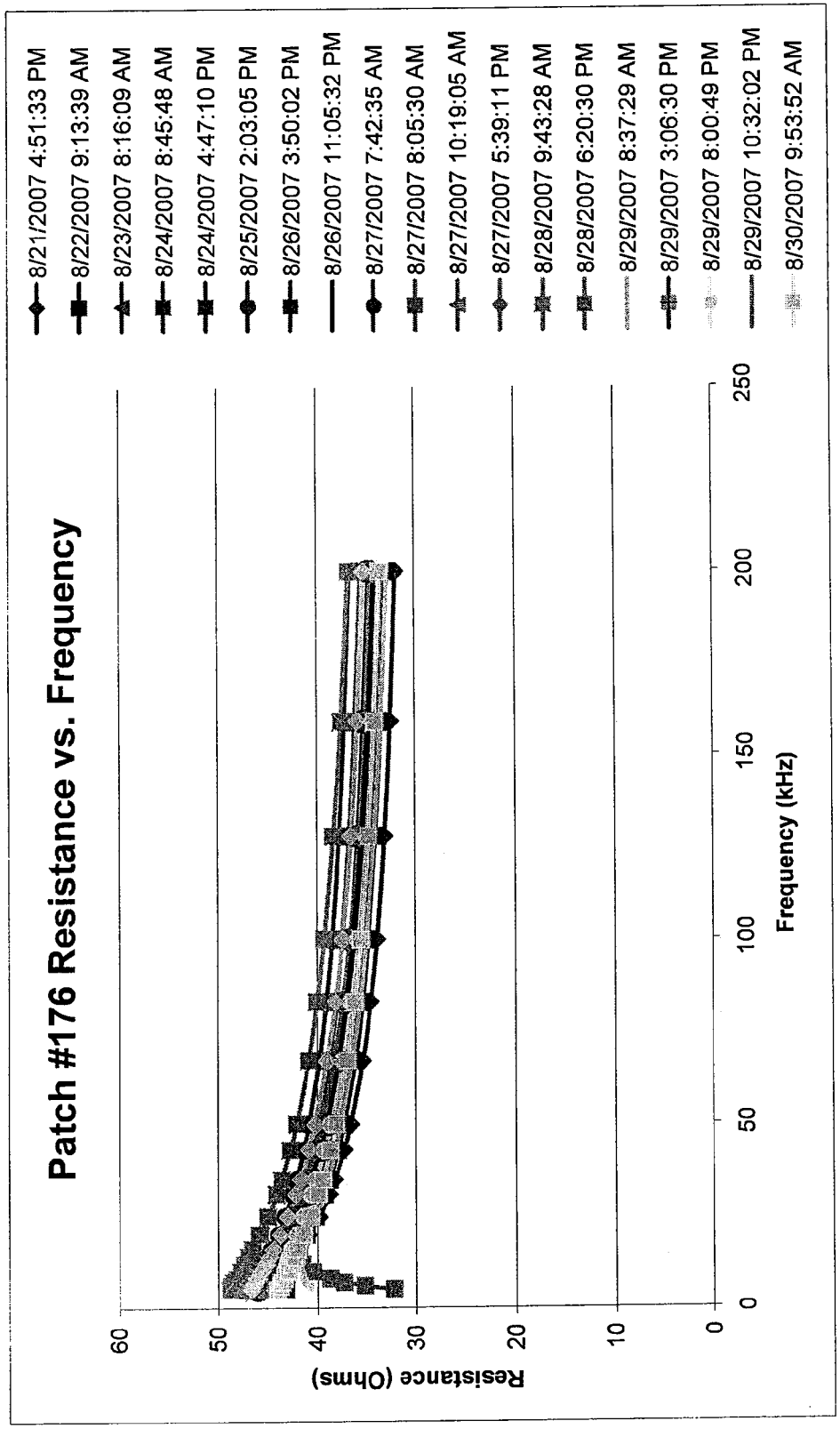
FIG. 6A shows a graph of measurements of tissue resistance over a range of measurement frequencies, in accordance with embodiments of the present invention.
Figure 6B:
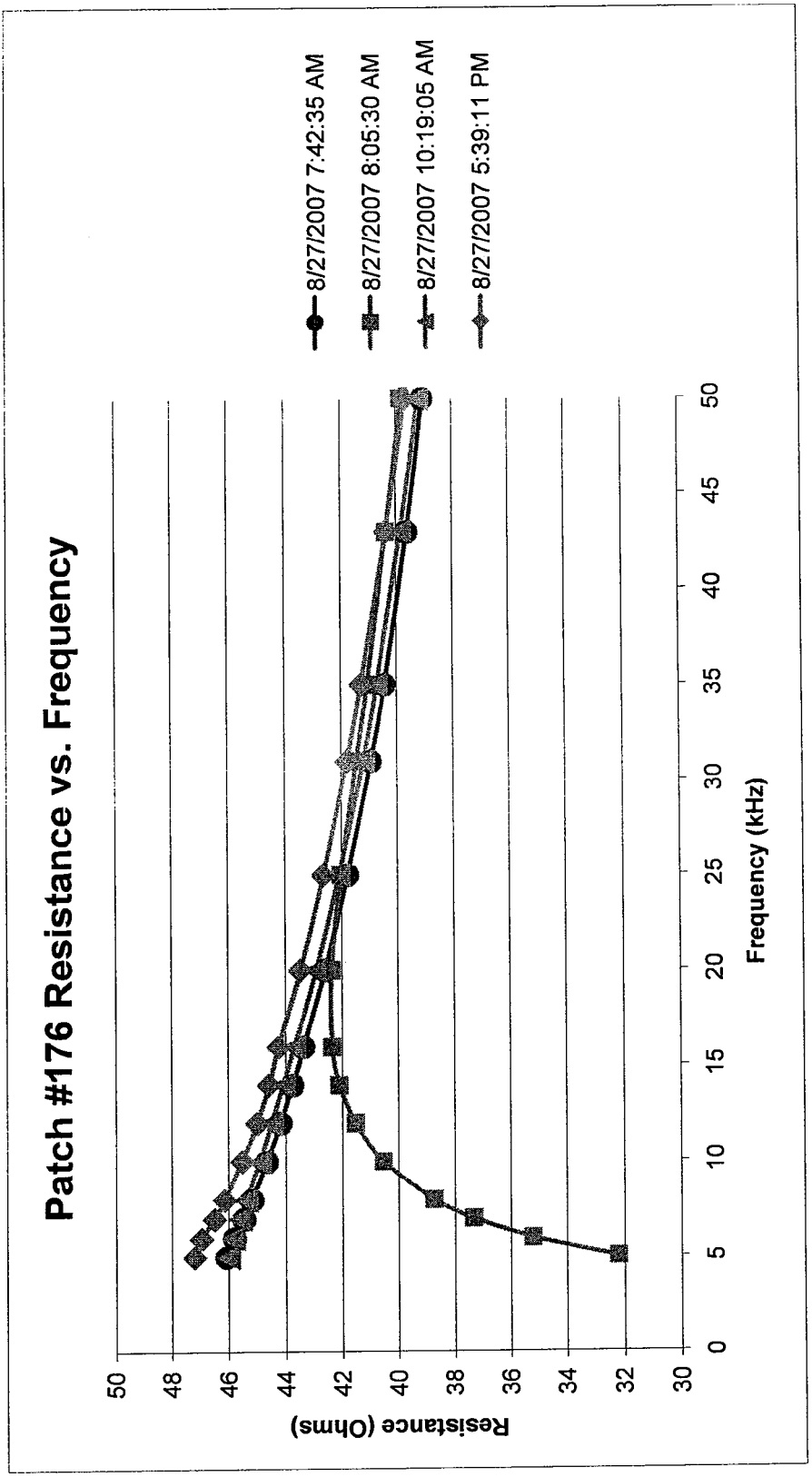
FIG. 6B shows a portion of the graph of FIG. 6A enlarged.

In at least some embodiments, resistance at low frequencies, for example less than 10 kHz, can be used to determine the quality of impedance measurements. For example, when a shower is taken the resistance may decrease, or droop, at lower frequencies but remain consistent at higher frequencies, which indicates that the adherent device and/or patient are exposed to water. FIGS. 6A and 6B, described more fully herein below, illustrate the low frequency droop effect on the measured resistance.

In many embodiments, the adherent devices described herein may be used for 90 day monitoring, or more, and may comprise completely disposable components and/or reusable components, and can provide reliable data acquisition and transfer. In many embodiments, the patch is configured for patient comfort, such that the adherent patch can be worn and/or tolerated by the patient for extended periods, for example 90 days or more. The patch may be worn continuously for at least seven days, for example 14 days, and then replaced with another patch. Adherent devices with comfortable patches that can be worn for extended periods and in which patches can be replaced and the electronics modules reused are described in U.S. Pat. App. Nos. 60/972,537, entitled "Adherent Device with Multiple Physiological Sensors"; and 60/972,629, entitled "Adherent Device with Multiple Physiological Sensors", both filed on Sep. 14, 2007, the full disclosures of which have been previously incorporated herein by reference. In many embodiments, the adherent patch comprises a tape, which comprises a material, preferably breathable, with an adhesive, such that trauma to the patient skin can be minimized while the patch is worn for the extended period. The printed circuit board may comprise a flex printed circuit board that can flex with the patient to provide improved patient comfort.

FIG. 1A shows a patient P and a monitoring system 10. Patient P comprises a midline M, a first side S1, for example a right side, and a second side S2, for example a left side. Monitoring system 10 comprises an adherent device 100. Adherent device 100 can be adhered to a patient P at many locations, for example thorax T of patient P. In many embodiments, the adherent device may adhere to one side of the patient, from which side data can be collected. Work in relation with embodiments of the present invention suggests that location on a side of the patient can provide comfort for the patient while the device is adhered to the patient.

Monitoring system 10 includes components to transmit data to a remote center 106. Remote center 106 can be located in a different building from the patient, for example in the same town as the patient, and can be located as far from the patient as a separate continent from the patient, for example the patient located on a first continent and the remote center located on a second continent. Adherent device 100 can communicate wirelessly to an intermediate device 102, for example with a single wireless hop from the adherent device on the patient to the intermediate device. Intermediate device 102 can communicate with remote center 106 in many ways, for example with an internet connection and/or with a cellular connection. In many embodiments, monitoring system 10 comprises a distributed processing system with at least one processor comprising a tangible medium of device 100, at least one processor 102P of intermediate device 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Remote center 106 can be in communication with a health care provider 108A with a communication system 107A, such as the Internet, an intranet, phone lines, wireless and/or satellite phone. Health care provider 108A, for example a family member, can be in communication with patient P with a communication, for example with a two way communication system, as indicated by arrow 109A, for example by cell phone, email, landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the patient's thorax and contains sensing electrodes, battery, memory, logic, and wireless communication capabilities. In some embodiments, the patch can communicate with the remote center, via the intermediate device in the patient's home. In some embodiments, remote center 106 receives the patient data and applies a patient evaluation algorithm, for example the prediction algorithm to predict cardiac decompensation. In some embodiments, the algorithm may comprise an algorithm to predict impending cardiac decompensation is described in U.S. Pat. App. No. 60/972,512, the full disclosure of which has been previously incorporated herein by reference. When a flag is raised, the center may communicate with the patient, hospital, nurse, and/or physician to allow for therapeutic intervention, for example to prevent decompensation.

The adherent device may be affixed and/or adhered to the body in many ways. For example, with at least one of the following an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide|remove old patch|place new patch|remove guide), or a keyed attachment for chatter reduction. The patch and/or device may comprise an adhesiveless embodiment (e.g. chest strap), and/or a low-irritation adhesive for sensitive skin. The adherent patch and/or device can comprise many shapes, for example at least one of a dogbone, an hourglass, an oblong, a circular or an oval shape.

In many embodiments, the adherent device may comprise a reusable electronics module with replaceable patches, and each of the replaceable patches may include a battery. The module may collect cumulative data for approximately 90 days and/or the entire adherent component (electronics+ patch) may be disposable. In a completely disposable embodiment, a "baton" mechanism may be used for data transfer and retention, for example baton transfer may include baseline information. In some embodiments, the device may have a rechargeable module, and may use dual battery and/or electronics modules, wherein one module 101A can be recharged using a charging station 103 while the other module 101B is placed on the adherent patch with connectors. In some embodiments, the intermediate device 102 may comprise the charging module, data transfer, storage and/or transmission, such that one of the electronics modules can be placed in the intermediate device for charging and/or data transfer while the other electronics module is worn by the patient.

System 10 can perform the following functions: initiation, programming, measuring, storing, analyzing, communicating, predicting, and displaying. The adherent device may contain a subset of the following physiological sensors: bioimpedance, respiration, respiration rate variability, heart rate (ave, min, max), heart rhythm, hear rate variability (HRV), heart rate turbulence (HRT), heart sounds (e.g. S3), respiratory sounds, blood pressure, activity, posture, wake/sleep, orthopnea, temperature/heat flux, and weight. The activity sensor may comprise one or more of the following: ball switch, accelerometer, minute ventilation, HR, bioimpedance noise, skin temperature/heat flux, BP, muscle noise, posture.

The adherent device can wirelessly communicate with remote center 106. The communication may occur directly (via a cellular or Wi-Fi network), or indirectly through intermediate device 102. Intermediate device 102 may consist of multiple devices, which can communicate wired or wirelessly to relay data to remote center 106.

In many embodiments, instructions are transmitted from remote site 106 to a processor supported with the adherent patch on the patient, and the processor supported with the patient can receive updated instructions for the patient treatment and/or monitoring, for example while worn by the patient.

FIG. 1B shows a bottom view of adherent device 100 as in FIG. 1A comprising an adherent patch 110. Adherent patch 110 comprises a first side, or a lower side 110A, that is oriented toward the skin of the patient when placed on the patient. In many embodiments, adherent patch 110 comprises a tape 110T which is a material, preferably breathable, with an adhesive 116A. Patient side 110A comprises adhesive 116A to adhere the patch 110 and adherent device 100 to patient P. Electrodes 112A, 112B, 112C and 112D are affixed to adherent patch 110. In many embodiments, at least four electrodes are attached to the patch, for example six electrodes. In some embodiments the patch comprises two electrodes, for example two electrodes to measure the electrocardiogram (ECG) of the patient. Gel 114A, gel 114B, gel 114C and gel 114D can each be positioned over electrodes 112A, 112B, 112C and 112D, respectively, to provide electrical conductivity between the electrodes and the skin of the patient. In many embodiments, the electrodes can be affixed to the patch 110, for example with known methods and structures such as rivets, adhesive, stitches, etc. In many embodiments, patch 110 comprises a breathable material to permit air and/or vapor to flow to and from the surface of the skin.

Figure 1C:
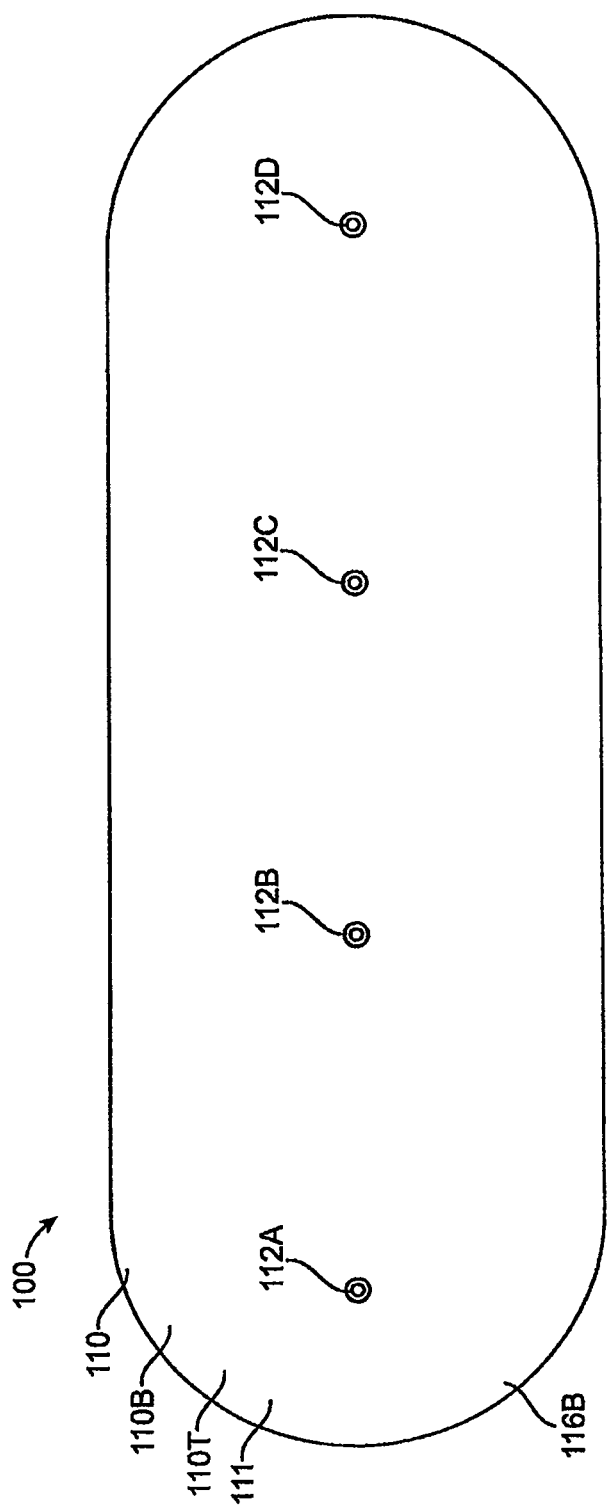
FIG. 1C shows a top view of the adherent patch, as in FIG. 1B.

FIG. 1C shows a top view of the adherent patch 100, as in FIG. 1B. Adherent patch 100 comprises a second side, or upper side 110B. In many embodiments, electrodes 112A, 112B, 112C and 112D extend from lower side 110A through adherent patch 110 to upper side 110B. An adhesive 116B can be applied to upper side 110B to adhere structures, for example a breathable cover, to the patch such that the patch can support the electronics and other structures when the patch is adhered to the patient. The PCB may comprise completely flex PCB, rigid PCB, rigid PCB combined flex PCB and/or rigid PCB boards connected by cable.

FIG. 1D shows a printed circuit boards and electronic components over adherent patch 110, as in FIG. 1A to 1C. In some embodiments, a printed circuit board (PCB), for example flex printed circuit board 120, may be connected to electrodes 112A, 112B, 112C and 112D with connectors 122A, 122B, 122C and 122D. Flex printed circuit board 120 can include traces 123A, 123B, 123C and 123D that extend to connectors 122A, 122B, 122C and 122D, respectively, on the flex PCB. Connectors 122A, 122B, 122C and 122D can be positioned on flex printed circuit board 120 in alignment with electrodes 112A, 112B, 112C and 112D so as to electrically couple the flex PCB with the electrodes. In some embodiments, connectors 122A, 122B, 122C and 122D may comprise insulated wires and/or a film with conductive ink that provide strain relief between the PCB and the electrodes. For example, connectors 122A, 122B, 122C and 122D may comprise a flexible polyester film coated with conductive silver ink. In some embodiments, additional PCB's, for example rigid PCB's 120A, 120B, 120C and 120D, can be connected to flex printed circuit board 120. Electronic components 130 can be connected to flex printed circuit board 120 and/or mounted thereon. In some embodiments, electronic components 130 can be mounted on the additional PCB's.

Electronic components 130 comprise components to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 comprise an activity sensor and activity circuitry 134, impedance circuitry 136 and electrocardiogram circuitry, for example ECG circuitry 136. In some embodiments, electronics circuitry 130 may comprise a microphone and microphone circuitry 142 to detect an audio signal from within the patient, and the audio signal may comprise a heart sound and/or a respiratory sound, for example an S3 heart sound and a respiratory sound with rales and/or crackles.

Electronics circuitry 130 may comprise a temperature sensor, for example a thermistor in contact with the skin of the patient, and temperature sensor circuitry 144 to measure a temperature of the patient, for example a temperature of the skin of the patient. A temperature sensor may be used to determine the sleep and wake state of the patient. The temperature of the patient can decrease as the patient goes to sleep and increase when the patient wakes up.

Work in relation to embodiments of the present invention suggests that skin temperature may effect impedance and/or hydration measurements, and that skin temperature measurements may be used to correct impedance and/or hydration measurements. In some embodiments, increase in skin temperature or heat flux can be associated with increased vasodilation near the skin surface, such that measured impedance measurement decreased, even through the hydration of the patient in deeper tissues under the skin remains substantially unchanged. Thus, use of the temperature sensor can allow for correction of the hydration signals to more accurately assess the hydration, for example extra cellular hydration, of deeper tissues of the patient, for example deeper tissues in the thorax.

Electronics circuitry 130 may comprise a processor 146. Processor 146 comprises a tangible medium, for example read only memory (ROM), electrically erasable programmable read only memory (EEPROM) and/or random access memory (RAM). Electronic circuitry 130 may comprise real time clock and frequency generator circuitry 148. In some embodiments, processor 136 may comprise the frequency generator and real time clock. The processor can be configured to control a collection and transmission of data from the impedance circuitry electrocardiogram circuitry and the accelerometer. In many embodiments, device 100 comprise a distributed processor system, for example with multiple processors on device 100.

In many embodiments, electronics components 130 comprise wireless communications circuitry 132 to communicate with remote center 106. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, wireless communication circuitry is configured to transmit the hydration signal, the electrocardiogram signal and the inclination signal to the remote center with a single wireless hop, for example from wireless communication circuitry 132 to intermediate device 102. The communication protocol comprises at least one of Bluetooth, Zigbee, WiFi, WiMax, IR, amplitude modulation or frequency modulation. In many embodiments, the communications protocol comprises a two way protocol such that the remote center is capable of issuing commands to control data collection.

Intermediate device 102 may comprise a data collection system to collect and store data from the wireless transmitter. The data collection system can be configured to communicate periodically with the remote center. The data collection system can transmit data in response to commands from remote center 106 and/or in response to commands from the adherent device.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer may comprises a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example ECG data and/or hydration data.

Impedance circuitry 136 can generate both hydration data and respiration data. In many embodiments, impedance circuitry 136 is electrically connected to electrodes 112A, 112B, 112C and 112D in a four pole configuration, such that electrodes 112A and 112D comprise outer electrodes that are driven with a current and comprise force electrodes that force the current through the tissue. The current delivered between electrodes 112A and 112D generates a measurable voltage between electrodes 112B and 112C, such that electrodes 112B and 112C comprise inner, sense, electrodes that sense and/or measure the voltage in response to the current from the force electrodes. In some embodiments, electrodes 112B and 112C may comprise force electrodes and electrodes 112A and 112B may comprise sense electrodes. The voltage measured by the sense electrodes can be used to measure the impedance of the patient and determine the respiration rate and/or hydration of the patient.

FIG. 1D1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to cardiac decompensation, and that extracellular resistance 158 and extracellular fluid can be effectively measured with frequencies in a range from about 0.5 kHz to about 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention measure hydration with frequencies from about 0.5 kHz to about 20 kHz to determine patient hydration.

In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from two or more of electrodes 112A, 112B, 112C and 112D in many ways. In some embodiments, ECG circuitry 138 is connected to inner electrodes 112B and 122C, which may comprise sense electrodes of the impedance circuitry as described above. In some embodiments, ECG circuitry 138 can be connected to electrodes 112A and 112D so as to increase spacing of the electrodes. The inner electrodes may be positioned near the outer electrodes to increase the voltage of the ECG signal measured by ECG circuitry 138. In many embodiments, the ECG circuitry may measure the ECG signal from electrodes 112A and 112D when current is not passed through electrodes 112A and 112D, for example with switches as described in U.S. App. No. 60/972,527, the full disclosure of which has been previously incorporated herein by reference.

Figure 1E:
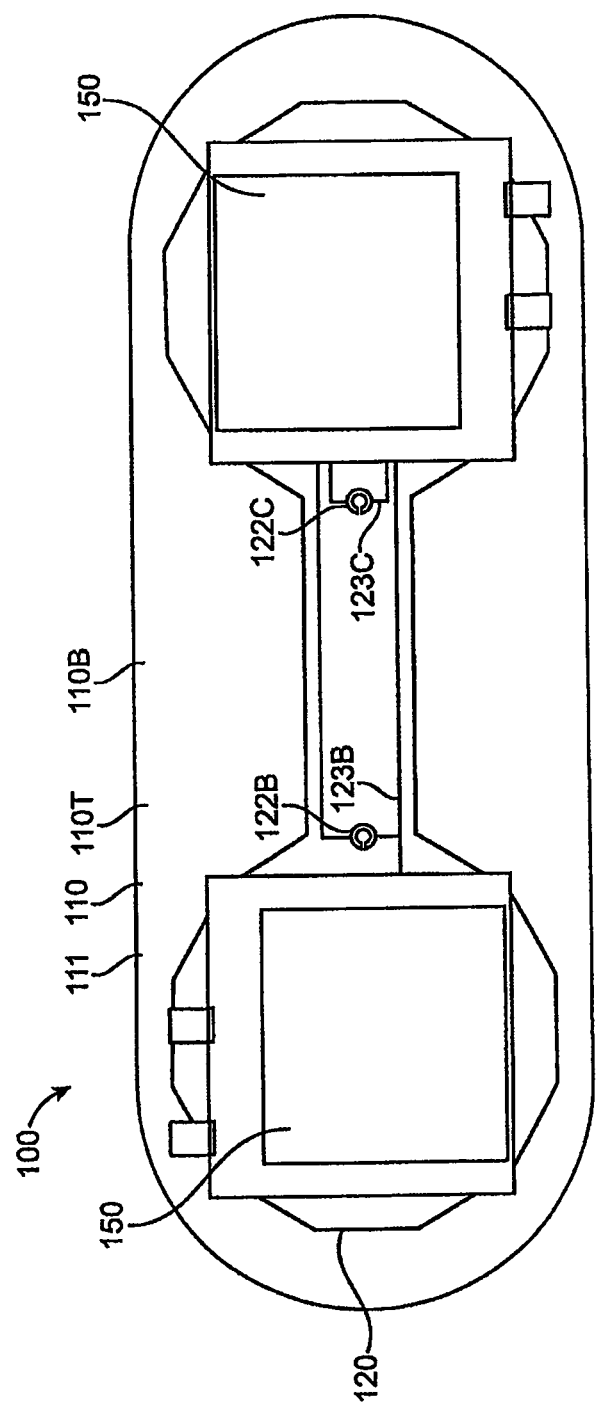
FIG. 1E shows batteries positioned over the printed circuit board and electronic components as in FIG. 1D.

FIG. 1E shows batteries 150 positioned over the flex printed circuit board and electronic components as in FIG. 1D. Batteries 150 may comprise rechargeable batteries that can be removed and/or recharged. In some embodiments, batteries 150 can be removed from the adherent patch and recharged and/or replaced.

Figure 1F:
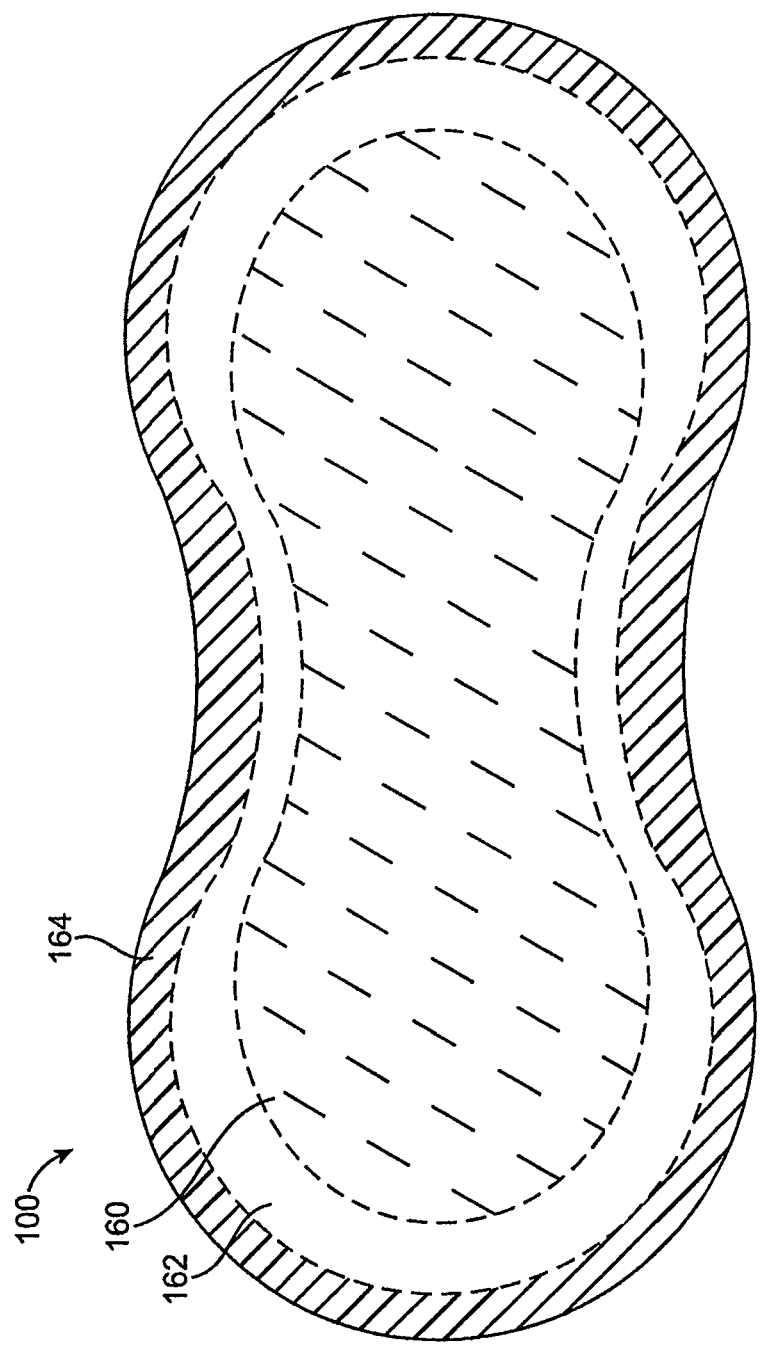
FIG. 1F shows a top view of an electronics housing and a breathable cover over the batteries, electronic components and printed circuit board as in FIG. 1E.

FIG. 1F shows a top view of a cover 162 over the batteries, electronic components and flex printed circuit board as in FIGS. 1A to 1E. In many embodiments, an electronics housing 160 may be disposed under cover 162 to protect the electronic components, and in some embodiments electronics housing 160 may comprise an encapsulant over the electronic components and PCB. In some embodiments, cover 162 can be adhered to adherent patch 110 with an adhesive 164 on an underside of cover 162. In many embodiments, electronics housing 160 may comprise a water proof material, for example a sealant adhesive such as epoxy or silicone coated over the electronics components and/or PCB. In some embodiments, electronics housing 160 may comprise metal and/or plastic. Metal or plastic may be potted with a material such as epoxy or silicone.

Cover 162 may comprise many known biocompatible cover, casing and/or housing materials, such as elastomers, for example silicone. The elastomer may be fenestrated to improve breathability. In some embodiments, cover 162 may comprise many known breathable materials, for example polyester, polyamide, and/or elastane (Spandex). The breathable fabric may be coated to make it water resistant, waterproof, and/or to aid in wicking moisture away from the patch.

Figure 1H:
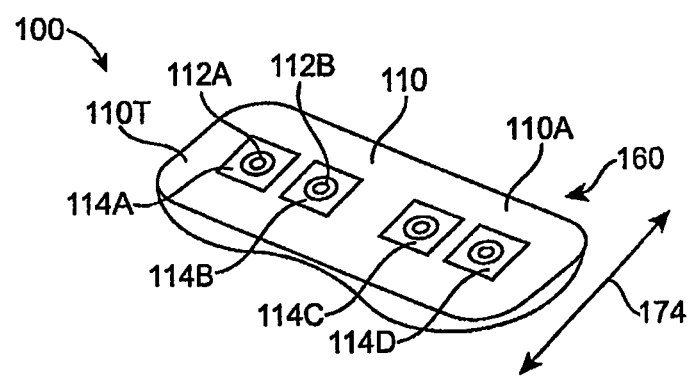
FIG. 1H shown a bottom isometric view of the adherent device as in FIGS. 1A to 1G.
Figure 1G:
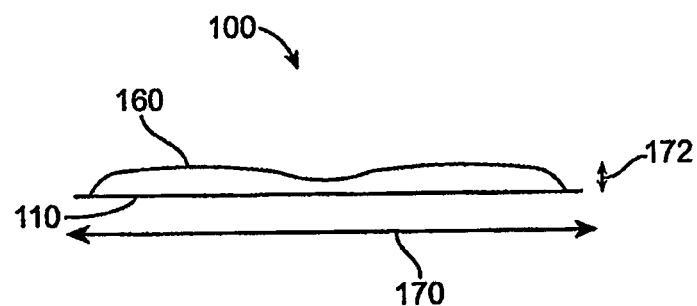
FIG. 1G shows a side view of the adherent device as in FIGS. 1A to 1F.

FIG. 1G shows a side view of adherent device 100 as in FIGS. 1A to 1F. Adherent device 100 comprises a maximum dimension, for example a length 170 from about 4 to 10 inches (from about 100 mm to about 250 mm), for example from about 6 to 8 inches (from about 150 mm to about 200 mm). In some embodiments, length 170 may be no more than about 6 inches (no more than about 150 mm). Adherent device 100 comprises a thickness 172. Thickness 172 may comprise a maximum thickness along a profile of the device. Thickness 172 can be from about 0.2 inches to about 0.4 inches (from about 5 mm to about 10 mm), for example about 0.3 inches (about 7.5 mm).

FIG. 1H shown a bottom isometric view of adherent device 100 as in FIGS. 1A to 1G. Adherent device 100 comprises a width 174, for example a maximum width along a width profile of adherent device 100. Width 174 can be from about 2 to about 4 inches (from about 50 mm to 100 mm), for example about 3 inches (about 75 mm).

Figure 1K:
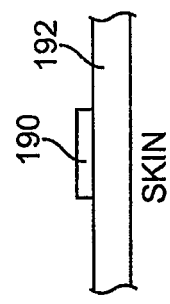
FIG. 1K shows at least one electrode configured to electrically couple to a skin of the patient through a breathable tape, according to embodiments of the present invention.
Figure 1I:
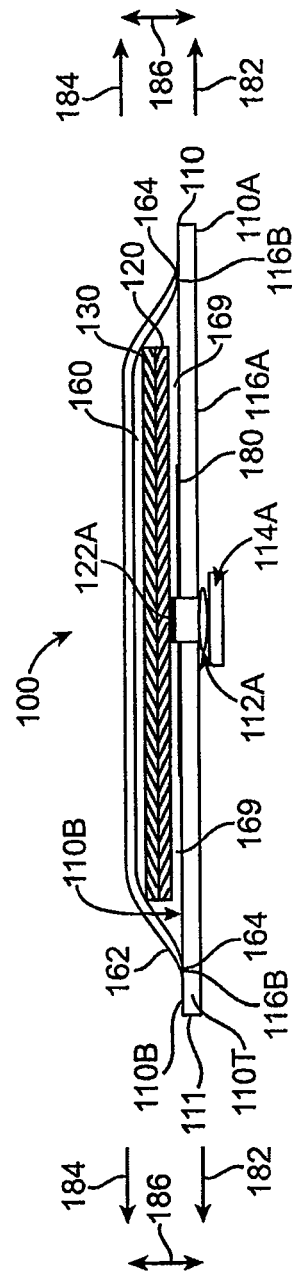
FIGS. 1I and 1J show a side cross-sectional view and an exploded view, respectively, of the adherent device as in FIGS. 1A to 1H.
Figure 1J:
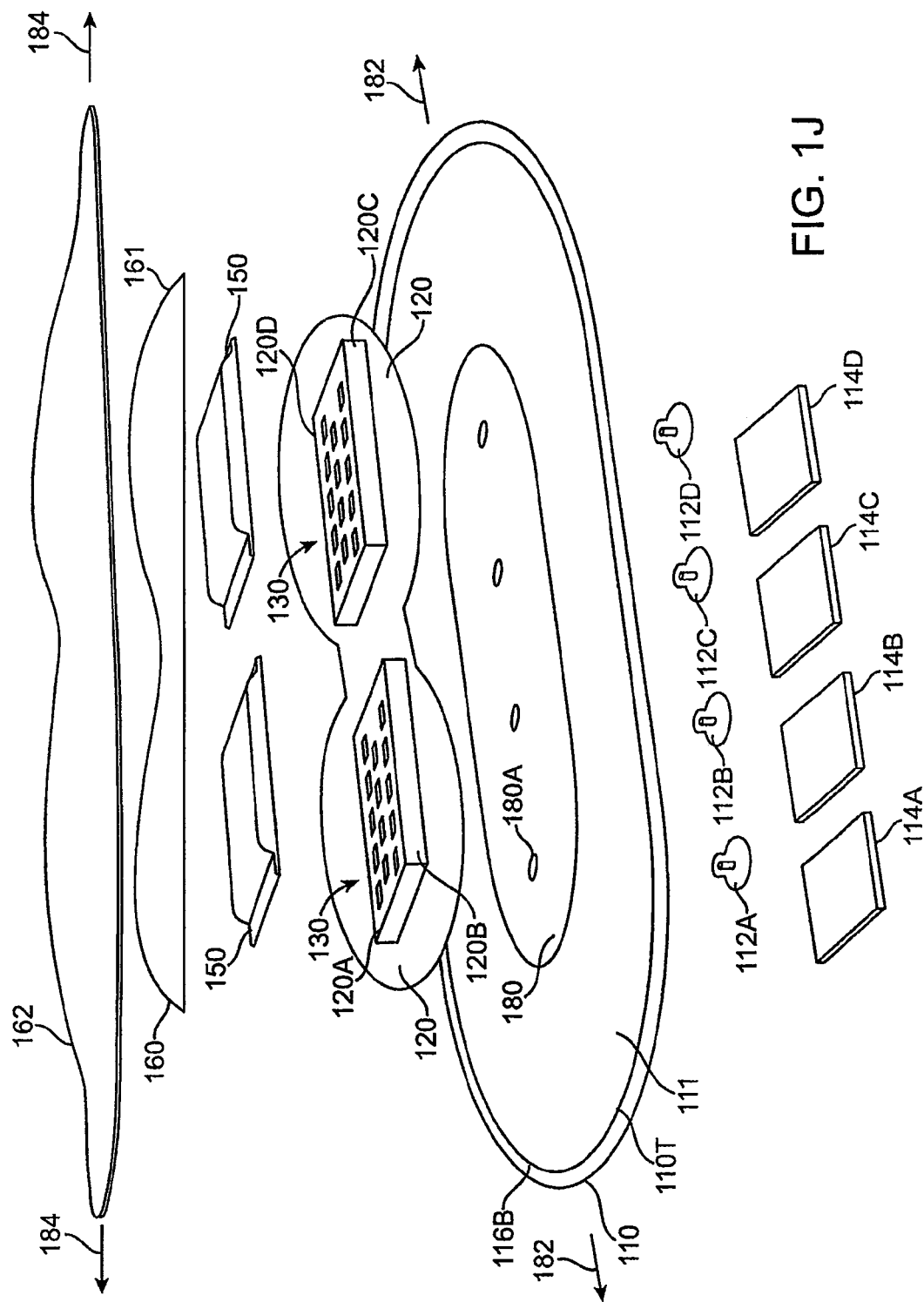

FIGS. 1I and 1J show a side cross-sectional view and an exploded view, respectively, of adherent device 100 as in FIGS. 1A to 1H. Device 100 comprises several layers. Gel 114A, or gel layer, is positioned on electrode 112A to provide electrical conductivity between the electrode and the skin. Electrode 112A may comprise an electrode layer. Adherent patch 110 may comprise a layer of breathable tape 110T, for example a known breathable tape, such as tricot-knit polyester fabric. An adhesive 116A, for example a layer of acrylate pressure sensitive adhesive, can be disposed on underside 110A of adherent patch 110.

A gel cover 180, or gel cover layer, for example a polyurethane non-woven tape, can be positioned over patch 110 comprising the breathable tape. A PCB layer, for example flex printed circuit board 120, or flex PCB layer, can be positioned over gel cover 180 with electronic components 130 connected and/or mounted to flex printed circuit board 120, for example mounted on flex PCB so as to comprise an electronics layer disposed on the flex PCB layer. In many embodiments, the adherent device may comprise a segmented inner component, for example the PCB may be segmented to provide at least some flexibility. In many embodiments, the electronics layer may be encapsulated in electronics housing 160 which may comprise a waterproof material, for example silicone or epoxy. In many embodiments, the electrodes are connected to the PCB with a flex connection, for example trace 123A of flex printed circuit board 120, so as to provide strain relive between the electrodes 112A, 112B, 112C and 112D and the PCB.

Gel cover 180 can inhibit flow of gel 114A and liquid. In many embodiments, gel cover 180 can inhibit gel 114A from seeping through breathable tape 110T to maintain gel integrity over time. Gel cover 180 can also keep external moisture, for example liquid water, from penetrating though the gel cover into gel 114A while allowing moisture vapor from the gel, for example moisture vapor from the skin, to transmit through the gel cover.

In many embodiments, cover 162 can encase the flex PCB and/or electronics and can be adhered to at least one of the electronics, the flex PCB or adherent patch 110, so as to protect at least the electronics components and the PCB. Cover 162 can attach to adherent patch 110 with adhesive 116B. Cover 162 can comprise many known biocompatible cover materials, for example silicone. Cover 162 can comprise an outer polymer cover to provide smooth contour without limiting flexibility. In many embodiments, cover 162 may comprise a breathable fabric. Cover 162 may comprise many known breathable fabrics, for example breathable fabrics as described above. In some embodiments, the breathable cover may comprise a breathable water resistant cover. In some embodiments, the breathable fabric may comprise polyester, nylon, polyamide, and/or elastane (Spandex) to allow the breathable fabric to stretch with body movement. In some embodiments, the breathable tape may contain and elute a pharmaceutical agent, such as an antibiotic, anti-inflammatory or antifungal agent, when the adherent device is placed on the patient.

The breathable cover 162 and adherent patch 110 comprise breathable tape can be configured to couple continuously for at least one week the at least one electrode to the skin so as to measure breathing of the patient. The breathable tape may comprise the stretchable breathable material with the adhesive and the breathable cover may comprises a stretchable water resistant material connected to the breathable tape, as described above, such that both the adherent patch and cover can stretch with the skin of the patient. Arrows 182 show stretching of adherent patch 110, and the stretching of adherent patch can be at least two dimensional along the surface of the skin of the patient. As noted above, connectors 122A, 122B, 122C and 122D between PCB 130 and electrodes 112A, 112B, 112C and 112D may comprise insulated wires that provide strain relief between the PCB and the electrodes, such that the electrodes can move with the adherent patch as the adherent patch comprising breathable tape stretches. Arrows 184 show stretching of cover 162, and the stretching of the cover can be at least two dimensional along the surface of the skin of the patient. Cover 162 can be attached to adherent patch 110 with adhesive 116B such that cover 162 stretches and/or retracts when adherent patch 110 stretches and/or retracts with the skin of the patient. For example, cover 162 and adherent patch 110 can stretch in two dimensions along length 170 and width 174 with the skin of the patient, and stretching along length 170 can increase spacing between electrodes. Stretching of the cover and adherent patch 110, for example in two dimensions, can extend the time the patch is adhered to the skin as the patch can move with the skin such that the patch remains adhered to the skin Electronics housing 160 can be smooth and allow breathable cover 162 to slide over electronics housing 160, such that motion and/or stretching of cover 162 is slidably coupled with housing 160. The printed circuit board can be slidably coupled with adherent patch 110 that comprises breathable tape 110T, such that the breathable tape can stretch with the skin of the patient when the breathable tape is adhered to the skin of the patient, for example along two dimensions comprising length 170 and width 174. Electronics components 130 can be affixed to printed circuit board 120, for example with solder, and the electronics housing can be affixed over the PCB and electronics components, for example with dip coating, such that electronics components 130, printed circuit board 120 and electronics housing 160 are coupled together. Electronics components 130, printed circuit board 120, and electronics housing 160 are disposed between the stretchable breathable material of adherent patch 110 and the stretchable water resistant material of cover 160 so as to allow the adherent patch 110 and cover 160 to stretch together while electronics components 130, printed circuit board 120, and electronics housing 160 do not stretch substantially, if at all. This decoupling of electronics housing 160, printed circuit board 120 and electronic components 130 can allow the adherent patch 110 comprising breathable tape to move with the skin of the patient, such that the adherent patch can remain adhered to the skin for an extended time of at least one week, for example two or more weeks.

An air gap 169 may extend from adherent patch 110 to the electronics module and/or PCB, so as to provide patient comfort. Air gap 169 allows adherent patch 110 and breathable tape 110T to remain supple and move, for example bend, with the skin of the patient with minimal flexing and/or bending of printed circuit board 120 and electronic components 130, as indicated by arrows 186. Printed circuit board 120 and electronics components 130 that are separated from the breathable tape 110T with air gap 169 can allow the skin to release moisture as water vapor through the breathable tape, gel cover, and breathable cover. This release of moisture from the skin through the air gap can minimize, and even avoid, excess moisture, for example when the patient sweats and/or showers.

The breathable tape of adherent patch 110 may comprise a first mesh with a first porosity and gel cover 180 may comprise a breathable tape with a second porosity, in which the second porosity is less than the first porosity to minimize, and even inhibit, flow of the gel through the breathable tape. The gel cover may comprise a polyurethane film with the second porosity.

In many embodiments, the adherent device comprises a patch component and at least one electronics module. The patch component may comprise adherent patch 110 comprising the breathable tape with adhesive coating 116A, at least one electrode, for example electrode 114A and gel 114. The at least one electronics module can be separable from the patch component. In many embodiments, the at least one electronics module comprises the flex printed circuit board 120, electronic components 130, electronics housing 160 and cover 162, such that the flex printed circuit board, electronic components, electronics housing and cover are reusable and/or removable for recharging and data transfer, for example as described above. In many embodiments, adhesive 116B is coated on upper side 110A of adherent patch 110B, such that the electronics module can be adhered to and/or separated from the adhesive component. In specific embodiments, the electronic module can be adhered to the patch component with a releasable connection, for example with Velcro™, a known hook and loop connection, and/or snap directly to the electrodes. In many embodiments, two electronics modules can be provided, such that one electronics module can be worn by the patient while the other is charged, as described above. Monitoring with multiple adherent patches for an extended period is described in U.S. Pat. App. No. 60/972,537, the full disclosure of which has been previously incorporated herein by reference. Many patch components can be provided for monitoring over the extended period. For example, about 12 patches can be used to monitor the patient for at least 90 days with at least one electronics module, for example with two reusable electronics modules.

At least one electrode 112A can extend through at least one aperture 180A in the breathable tape 110 and gel cover 180.

In some embodiments, the adhesive patch may comprise a medicated patch that releases a medicament, such as antibiotic, beta-blocker, ACE inhibitor, diuretic, or steroid to reduce skin irritation. The adhesive patch may comprise a thin, flexible, breathable patch with a polymer grid for stiffening. This grid may be anisotropic, may use electronic components to act as a stiffener, may use electronics-enhanced adhesive elution, and may use an alternating elution of adhesive and steroid.

FIG. 1K shows at least one electrode 190 configured to electrically couple to a skin of the patient through a breathable tape 192. In many embodiments, at least one electrode 190 and breathable tape 192 comprise electrodes and materials similar to those described above. Electrode 190 and breathable tape 192 can be incorporated into adherent devices as described above, so as to provide electrical coupling between the skin an electrode through the breathable tape, for example with the gel.

Figure 2A:
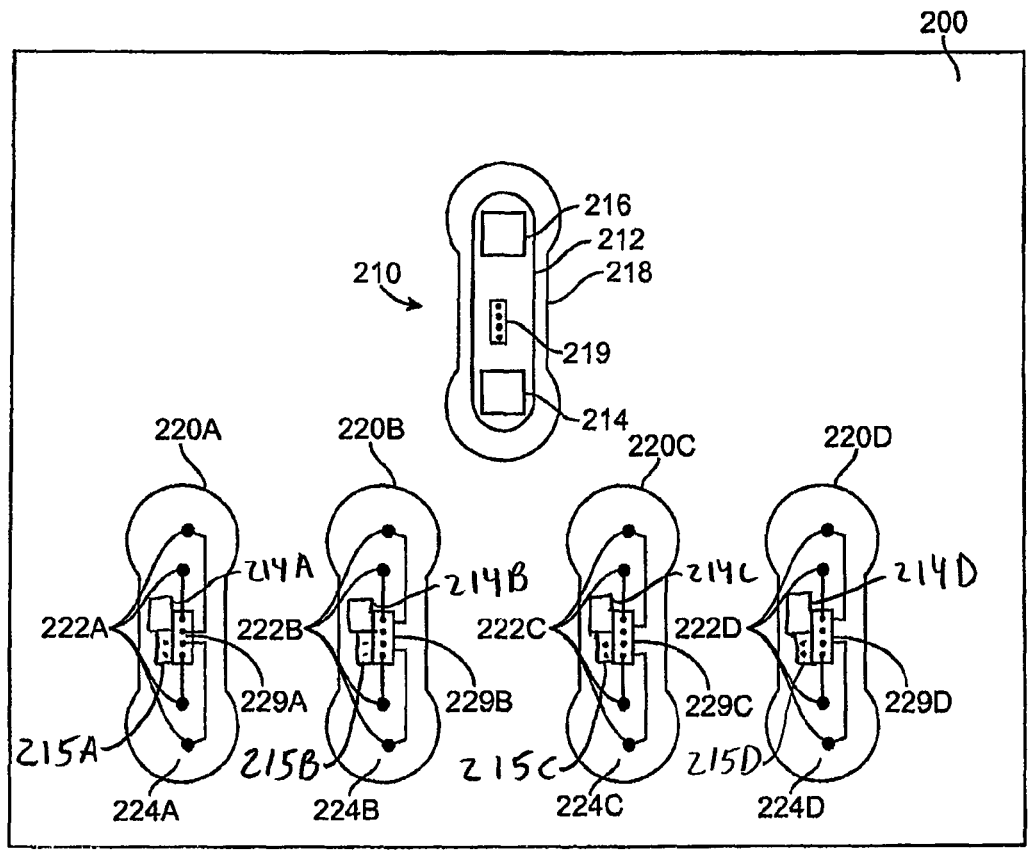
FIGS. 2A to 2C show a system to monitor a patient for an extended period comprising a reusable electronic component and a plurality of disposable patch components, according to embodiments of the present invention.
Figure 2B:
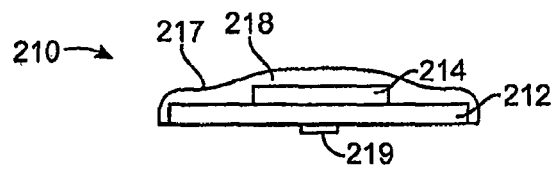
Figure 2C:
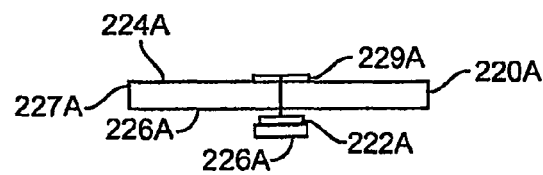

FIGS. 2A to 2C show a schematic illustration of a system 200 to monitor a patient for an extended period. FIG. 2A shows a schematic illustration of system 200 comprising a reusable electronics module 210 and a plurality of disposable patch components comprising a first disposable patch component 220A, a second disposable patch component 220B, a third disposable patch component 220C and a fourth disposable patch component 220D. Although four patch components a shown the plurality may comprise as few as two patch component and as many as three or more patch components, for example 25 patch components.

FIG. 2B shows a schematic illustration of a side cross-sectional view of reusable electronics module 210. Reusable electronics module 210 may comprises many of the structures described above that may comprise the electronics module. In many embodiments, reusable electronics module 210 comprises a PCB, for example a flex PCB 212, electronics components 216, batteries 216, and a cover 217, for example as described above. In some embodiments, reusable electronics module 210 may comprise an electronics housing over the electronics components and/or PCB as described above. The electronics components may comprise circuitry and/or sensors for measuring ECG signals, hydration impedance signals, respiration impedance signals and accelerometer signals, for example as described above. In many embodiments, reusable electronics module 210 comprises a connector 219 adapted to connect to each of the disposable patch components, sequentially, for example one disposable patch component at a time. Connector 219 can be formed in many ways, and may comprise known connectors as described above, for example a snap. In some embodiments, the connectors on the electronics module and adhesive component can be disposed at several locations on the reusable electronics module and disposable patch component, for example near each electrode, such that each electrode can couple directly to a corresponding location on the flex PCB of the reusable electronics component.

Alternatively or in combination with batteries 216, each of the plurality of disposable patch components may comprise a disposable battery. For example first disposable patch component 220A may comprise a disposable battery 214A; second disposable patch component 220B may comprise a disposable battery 214B; third disposable patch component 220C may comprise a disposable battery 214C; and a fourth disposable patch component 220D may comprise a disposable battery 214D. Each of the disposable batteries, 214A, 214B, 214C and 214D may be affixed to each of disposable patches 220A, 220B, 220C and 220D, respectively, such that the batteries are adhered to the disposable patch component before, during and after the respective patch component is adhered to the patient. Each of the disposable batteries, 214A, 214B, 214C and 214D may be coupled to connectors 215A, 215B, 215C and 215D, respectively. Each of connectors 215A, 215B, 215C and 215D can be configured to couple to a connector of the reusable module 220, so as to power the reusable module with the disposable battery coupled thereto. Each of the disposable batteries, 214A, 214B, 214C and 214D may be coupled to connectors 215A, 215B, 215C and 215D, respectively, such that the batteries are not coupled to the electrodes of the respective patch component, so as to minimize, and even avoid, degradation of the electrodes and/or gel during storage when each disposable battery is adhered to each respective disposable patch component.

FIG. 2C shows a schematic illustration first disposable patch component 220A of the plurality of disposable patch components that is similar to the other disposable patch components, for example second disposable patch component 220B, third disposable patch component 220C and fourth disposable patch component 220C. The disposable patch component comprises a breathable tape 227A, an adhesive 226A on an underside of breathable tape 227A to adhere to the skin of the patient, and at least four electrodes 222A. The at least four electrodes 224A are configured to couple to the skin of a patient, for example with a gel 226A, in some embodiments the electrodes may extend through the breathable tape to couple directly to the skin of the patient with aid form the gel. In some embodiments, the at least four electrodes may be indirectly coupled to the skin through a gel and/or the breathable tape, for example as described above. A connector 229A on the upper side of the disposable adhesive component can be configured for attachment to connector 219 on reusable electronics module 210 so as to electrically couple the electrodes with the electronics module. The upper side of the disposable patch component may comprise an adhesive 224A to adhere the disposable patch component to the reusable electronics module. The reusable electronics module can be adhered to the patch component with many additional known ways to adhere components, for example with Velcro™ comprising hooks and loops, snaps, a snap fit, a lock and key mechanisms, magnets, detents and the like.

Figure 2D:
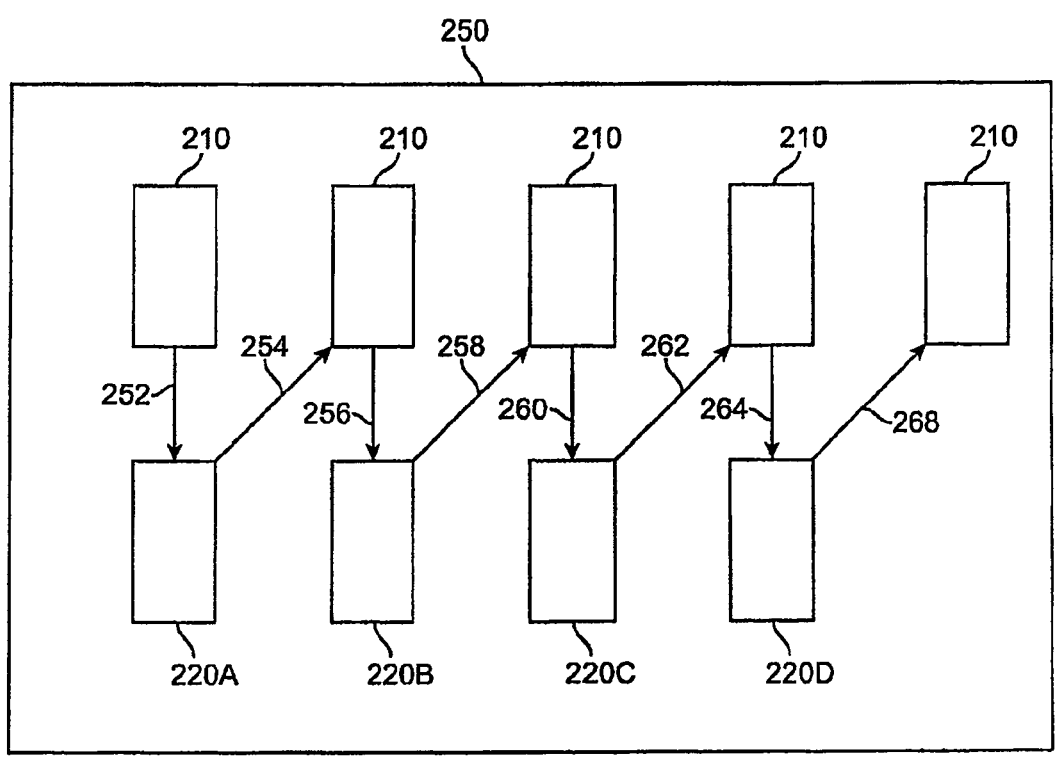
FIG. 2D shows a method of using the system as in FIGS. 2A to 2C.

FIG. 2D shows a method 250 of using system 200, as in FIGS. 2A to 2C. A step 252 adheres electronics module 210 to first disposable adherent patch component 220A of the plurality of adherent patch components and adheres the first disposable patch component to the skin of the patient, for example with the first adherent patch component adhered to the reusable electronics module. A step 254 removes the first disposable adherent patch from the patient and separates first disposable adherent patch component 220A from reusable electronics module 210. A step 256 adheres electronics module 210 to second disposable adherent patch component 220B and adheres the second disposable patch component to the skin of the patient, for example with the second adherent patch component adhered to the reusable electronics module. A step 258 removes the second disposable adherent patch from the patient and separates second disposable adherent patch component 220B from reusable electronics module 210. A step 260 adheres electronics module 210 to third disposable adherent patch component 220C and adheres the third disposable patch component to the skin of the patient, for example with the third adherent patch component adhered to the reusable electronics module. A step 262 removes the third disposable adherent patch from the patient and separates third disposable adherent patch component 220C from reusable electronics module 210. A step 264 adheres electronics module 210 to fourth disposable adherent patch component 220D and adheres the fourth disposable patch component to the skin of the patient, for example with the fourth adherent patch component adhered to the reusable electronics module. A step 268 removes the fourth disposable adherent patch from the patient and separates fourth disposable adherent patch component 220D from reusable electronics module 210.

In many embodiments, physiologic signals, for example ECG, hydration impedance, respiration impedance and accelerometer impedance are measured when the adherent patch component is adhered to the patient, for example when any of the first, second, third or fourth disposable adherent patches is adhered to the patient.

FIGS. 3A to 3D show a method 300 of monitoring a patient for an extended period with adherent patches alternatively adhered to a right side 302 and a left side 304 of the patient. Work in relation to embodiments of the present invention suggests that repeated positioning of a patch at the same location can irritate the skin and may cause patient discomfort. This can be avoided by alternating the patch placement between left and right sides of the patient, often a front left and a front right side of the patient where the patient can reach easily to replace the patch. In some embodiments, the patch location can be alternated on the same side of the patient, for example higher and/or lower on the same side of the patient without substantial overlap to allow the skin to recover and/or heal. In many embodiments, the patch can be symmetrically positioned on an opposite side such that signals may be similar to a previous position of the patch symmetrically disposed on an opposite side of the patient. In many embodiments, the duration between removal of one patch and placement of the other patch can be short, such that any differences between the signals may be assumed to be related to placement of the patch, and these differences can be removed with signal processing.

In many embodiments each patch comprises at least four electrodes configured to measure an ECG signal and impedance, for example hydration and/or respiration impedance. In many embodiments, the patient comprises a midline 304, with first side, for example right side 302, and second side, for example left side 306, symmetrically disposed about the midline. A step 310 adheres a first adherent patch 312 to at a first location 314 on a first side 302 of the patient for a first period of time, for example about 1 week. While the adherent patch 312 is position at first location 314 on the first side of the patient, the electrodes of the patch are coupled to the skin of the patient to measure the ECG signal and impedance signals.

A step 320 removes patch 312 and adheres a second adherent patch 322 at a second location 324 on a second side 206 of the patient for a second period of time, for example about 1 week. In many embodiments, second location 324 can be symmetrically disposed opposite first location 314 across midline 304, for example so as to minimize changes in the sequential impedance signals measured from the second side and first side. While adherent patch 322 is position at second location 324 on the second side of the patient, the electrodes of the patch are coupled to the skin of the patient to measure the ECG signal and impedance signals. In many embodiments, while adherent patch 322 is positioned at second location 324, skin at first location 314 can heal and recover from adherent coverage of the first patch. In many embodiments, second location 324 is symmetrically disposed opposite first location 314 across midline 304, for example so as to minimize changes in the impedance signals measured between the first side and second side. In many embodiments, the duration between removal of one patch and placement of the other patch can be short, such that any differences between the signals may be assumed to be related to placement of the patch, and these differences can be removed with signal processing.

A step 330 removes second patch 322 and adheres a third adherent patch 332 at a third location 334 on the first side, for example right side 302, of the patient for a third period of time, for example about 1 week. In many embodiments, third location 334 can be symmetrically disposed opposite second location 324 across midline 304, for example so as to minimize changes in the sequential impedance signals measured from the third side and second side. In many embodiments, third location 334 substantially overlaps with first location 314, so as to minimize differences in measurements between the first adherent patch and third adherent patch that may be due to patch location. While adherent patch 332 is positioned at third location 334 on the first side of the patient, the electrodes of the patch are coupled to the skin of the patient to measure the ECG signal and impedance signals. In many embodiments, while adherent patch 332 is positioned at third location 334, skin at second location 324 can heal and recover from adherent coverage of the second patch. In many embodiments, the duration between removal of one patch and placement of the other patch can be short, such that any differences between the signals may be assumed to be related to placement of the patch, and these differences can be removed with signal processing.

A step 340 removes third patch 332 and adheres a fourth adherent patch 342 at a fourth location 344 on the second side, for example left side 306, of the patient for a fourth period of time, for example about 1 week. In many embodiments, fourth location 344 can be symmetrically disposed opposite third location 334 across midline 304, for example so as to minimize changes in the sequential impedance signal measured from the fourth side and third side. In many embodiments, fourth location 344 substantially overlaps with second location 324, so as to minimize differences in measurements between the second adherent patch and fourth adherent patch that may be due to patch location. While adherent patch 342 is positioned at fourth location 344 on the second side of the patient, the electrodes of the patch are coupled to the skin of the patient to measure the ECG signal and impedance signals. In many embodiments, while adherent patch 342 is positioned at fourth location 324, skin at third location 334 can heal and recover from adherent coverage of the third patch. In many embodiments, the duration between removal of one patch and placement of the other patch can be short, such that any differences between the signals may be assumed to be related to placement of the patch, and these differences can be removed with signal processing.

It should be appreciated that the specific steps illustrated in FIGS. 3A to 3D provide a particular method of monitoring a patient for an extended period, according to an embodiment of the present invention. Other sequences of steps may also be performed according to alternative embodiments. For example, alternative embodiments of the present invention may perform the steps outlined above in a different order. Moreover, the individual steps illustrated in FIGS. 3A to 3D may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 4A:
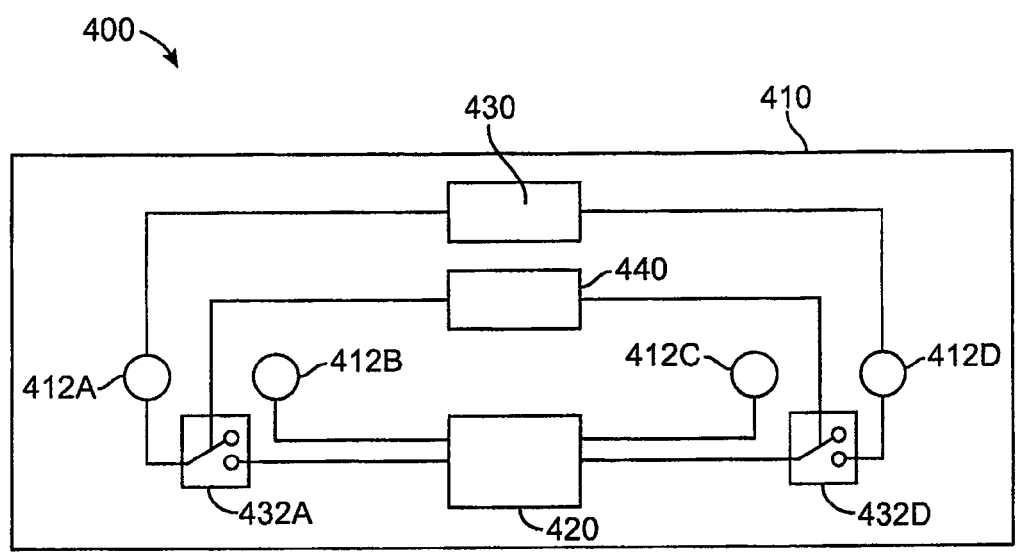
FIG. 4A shows an adherent device to measure an impedance signal and an electrocardiogram signal, according to embodiments of the present invention.

FIG. 4A shows a monitoring system 400 comprising an adherent device 410 to measure an impedance signal and an electrocardiogram signal. Device 410 may comprise wireless communication circuitry, accelerometer sensors and/or circuitry and many sensors and electronics components and structures as described above. Adherent device 410 comprises at least four electrodes. In many embodiments, the at least four electrodes comprises four electrodes, for example a first electrode 412A, a second electrode 412B, a third electrode 412C and a fourth electrode 412D. Work in relation to embodiments of the present invention suggests that embodiments in which the at least four electrodes comprises four electrodes can decrease a footprint, or size, of the device on the patient and may provide improved patient comfort. In many embodiments, first electrode 412A and fourth electrode 412D comprise outer electrodes, and second electrode 412B and third electrode 412C comprise inner electrodes, for example in embodiments where the electrodes are arranged in an elongate pattern.

Adherent device 410 comprises impedance circuitry 420 that can be used to measure hydration and respiration of the patient, and ECG circuitry 430 that is used to measure an electrocardiogram signal of the patient. Impedance circuitry 420 comprises force circuitry connected to the outer electrodes to drive a current between the electrodes. Impedance circuitry 420 comprises sense circuitry to measure a voltage between the inner electrodes resulting from the current passed between the outer force electrodes, such that the impedance of the tissue can be determined. Impedance circuitry 420 may comprise known 4-pole, or quadrature, low power circuitry. ECG circuitry 430 can be connected to the outer electrodes, or force electrodes, to measure an ECG signal. Work in relation to embodiments of the present invention suggests that this use of the outer electrodes can increase the ECG signal as compared to the inner electrodes, in some embodiments, that may be due to the increased distance between the outer electrodes. ECG circuitry 430 may comprise known ECG circuitry and components, for example low power instrumentation and/or operational amplifiers.

In many embodiments, electronic switch 432A and electronic switch 432D are connected in series between impedance circuitry 420 and electrode 412A and 412D, respectively. In many embodiments, electronic switch 432A and electronic switch 432D open such that the outer electrodes can be isolated from the impedance circuitry when the ECG circuitry measures ECG signals. When electronic switch 432A and electronic switch 432D are closed, impedance circuitry 420 can force electrical current through the outer electrodes to measure impedance. In many embodiments, electronic switch 432A and electronic switch 432D can be located in the same packaging, and may comprise CMOS, precision, analog switches with low power consumption, low leakage currents, and fast switching speeds.

A processor 440 can be connected to electronic switch 423A, electronic switch 432D, impedance circuitry 420 and ECG circuitry 430 to control measurement of the ECG and impedance signals. Processor 430 comprises a tangible medium, for example read only memory (ROM), electrically erasable programmable read only memory (EEPROM) and/or random access memory (RAM). In many embodiments, processor 440 controls the measurements such that the measurements from impedance circuitry 420 and ECG circuitry 430 are time division multiplexed in response to control signals from processor 440.

Figure 4B:
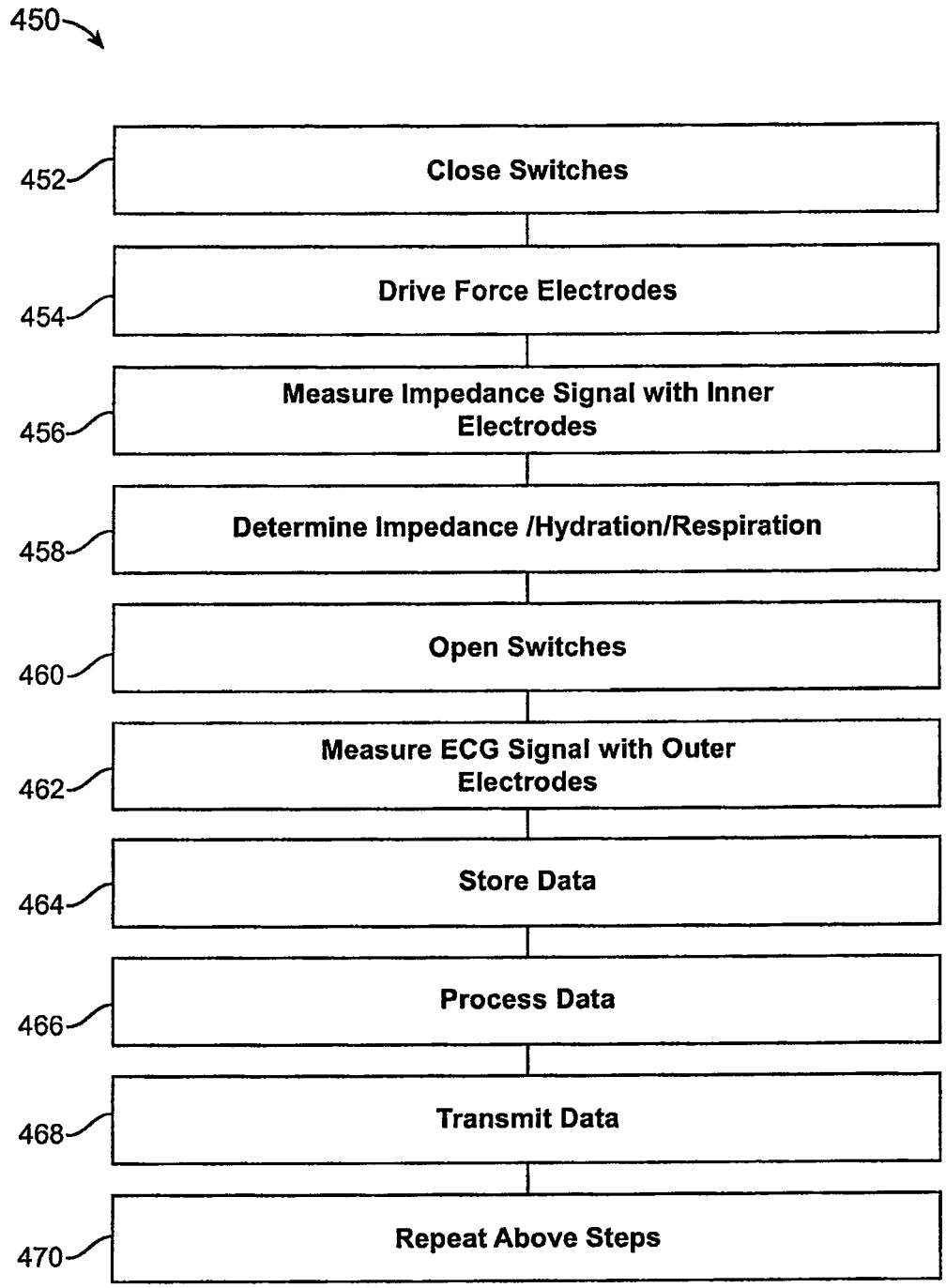
FIG. 4B shows a method of measuring the impedance signal and the electrocardiogram signal, according to embodiments of the present invention.

FIG. 4B shows a method 450 of measuring the impedance signal and the electrocardiogram signal with processor 440. A step 452 closes the switches. A step 454 drives the force electrodes. A step 456 measures the impedance signal with the inner electrodes. A step 458 determines the impedance, hydration and/or respiration from the impedance signal. A step 460 opens the switches. A step 462 measures the ECG signal with the outer electrodes. A step 464 stores the data from the impedance signals and ECG signals. A step 466 processes the data. A step 468 transmits the data, for example wirelessly to the remove center. A step 470 repeats the above steps.

It should be appreciated that the specific steps illustrated in FIG. 4B provide a particular method of measuring signals, according to an embodiment of the present invention. Other sequences of steps may also be performed according to alternative embodiments. For example, alternative embodiments of the present invention may perform the steps outlined above in a different order. Moreover, the individual steps illustrated in FIG. 4B may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 5A:
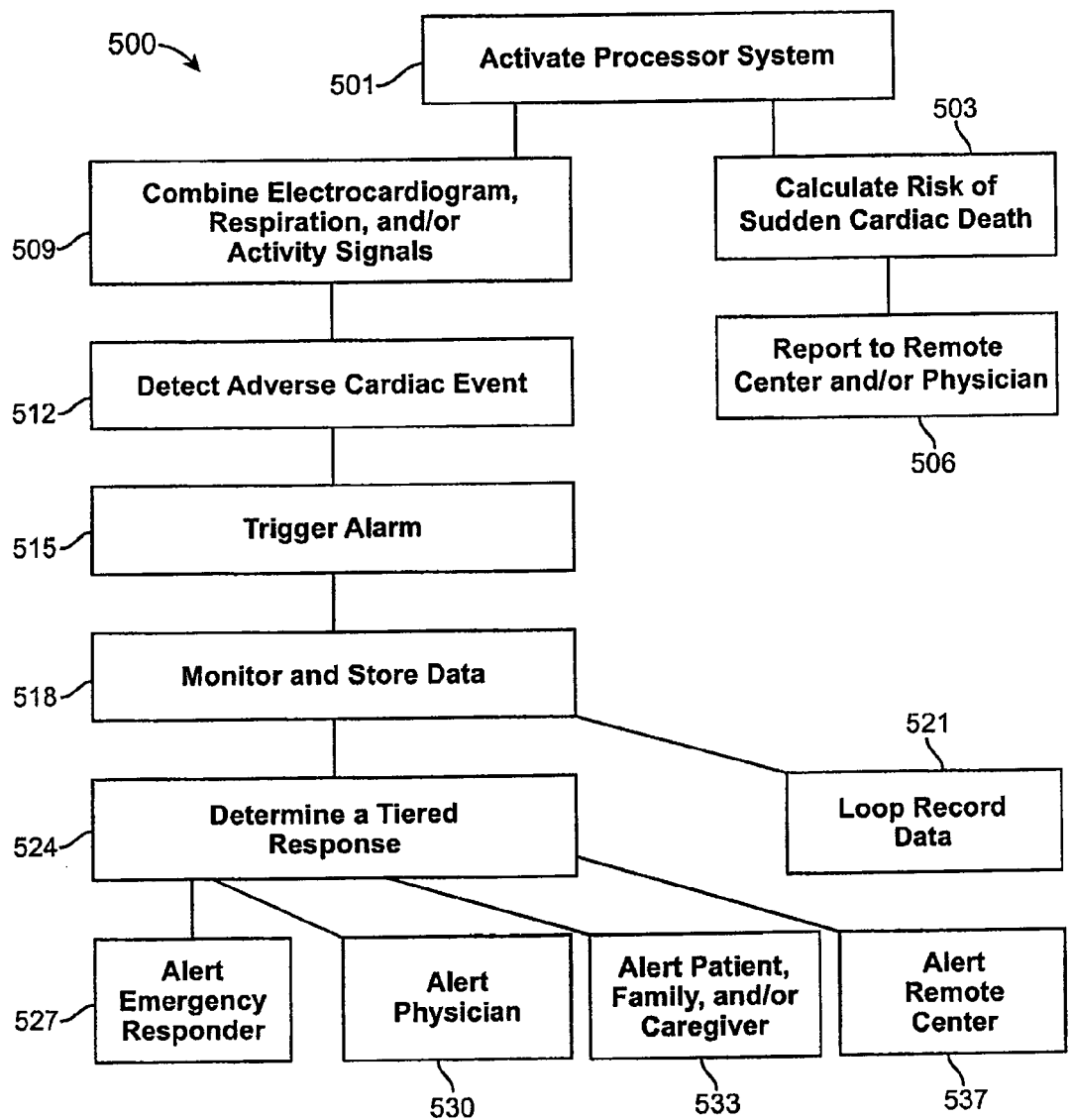
FIG. 5A shows a method for monitoring a patient and responding to a signal event.

FIG. 5A shows a method 500 for monitoring a patient and responding to a signal event. A step 501 activates a processor system. A step 503 calculates a risk of sudden cardiac death. A step 506 reports to a remote center and/or physician. A step 509 combines at least two of the electrocardiogram signal, respiration signal, and/or activity signals. A step 512 detects an adverse cardiac event. An adverse cardiac event may comprise an atrial fibrillation in response to the electrocardiogram signal and/or an acute myocardial infarction in response to an ST segment elevation of the electrocardiogram signal. A step 515 triggers an alarm. A step 518 continuously monitors and stores in tangible media at least two of the electrocardiogram signal, the respiration signal, or the activity signal. In some embodiments, a step may also comprise monitoring a high risk patent post myocardial infarction with the at least two of the electrocardiogram signal, the respiration signal or the activity signal, and/or a bradycardia of the patient at risk for sudden death. The electrocardiogram signal may comprise at least one of a Brugada Syndrome with an ST elevation and a short QT interval or long-QT interval. A step 521 loop records the aforementioned data. A step 524 determines a tiered response. In many embodiments, the tiered response may comprise tiers, or levels, appropriate to the detected status of the patient. A step 527 comprises a first tier response which alerts an emergency responder. A step 530 comprises a second tier response which alerts a physician. A step 533 comprises a third tier response which alerts a patient, family, or caregiver. A step 537 comprises a fourth tier response which alerts a remote center. A tiered response may also comprise of wirelessly transmitting the at least two of the electro cardiogram signal, the respiration signal, or the activity signal with a single wireless hop from a wireless communication circuitry to an intermediate device.

The signals can be combined in many ways. In some embodiments, the signals can be used simultaneously to determine the impending cardiac decompensation.

In some embodiments, the signals can be combined by using the at least two of the electrocardiogram signal, the respiration signal or the activity signal to look up a value in a previously existing array.

TABLE 1

Lookup Table for ECG and Respiration Signals.

| Heart Rate/Respiration | A-B bpm | C-D bpm | E-F bpm |
|---|---|---|---|
| U-V per min | N | N | Y |
| W-X per min | N | Y | Y |
| Y-Z per min | Y | Y | Y |

Table 1 shows combination of the electrocardiogram signal with the respiration signal to look up a value in a pre-existing array. For example, at a heart rate in the range from A to B bpm and a respiration rate in the range from U to V per minute triggers a response of N. In some embodiments, the values in the table may comprise a tier or level of the response, for example four tiers. In specific embodiments, the values of the look up table can be determined in response to empirical data measured for a patient population of at least about 100 patients, for example measurements on about 1000 to 10,000 patients. The look up table shown in Table 1 illustrates the use of a look up table according to one embodiment, and one will recognize that many variables can be combined with a look up table.

In some embodiments, the table may comprise a three or more dimensional look up table, and the look up table may comprises a tier, or level, of the response, for example an alarm.

In some embodiments, the signals may be combined with at least one of adding, subtracting, multiplying, scaling or dividing the at least two of the electrocardiogram signal, the respiration signal or the activity signal. In specific embodiments, the measurement signals can be combined with positive and or negative coefficients determined in response to empirical data measured for a patient population of at least about 100 patients, for example data on about 1000 to 10,000 patients.

In some embodiments, a weighted combination may combine at least two measurement signals to generate an output value according to a formula of the general form $$\text{OUTPUT} = aX + bY$$

where a and b comprise positive or negative coefficients determined from empirical data and X, and Z comprise measured signals for the patient, for example at least two of the electrocardiogram signal, the respiration signal or the activity signal. While two coefficients and two variables are shown, the data may be combined with multiplication and/or division. One or more of the variables may be the inverse of a measured variable.

In some embodiments, the ECG signal comprises a heart rate signal that can be divided by the activity signal. Work in relation to embodiments of the present invention suggests that an increase in heart rate with a decrease in activity can indicate an impending decompensation. The signals can be combined to generate an output value with an equation of the general form $$\text{OUTPUT} = aX/Y + bZ$$

where X comprise a heart rate signal, Y comprises an activity signal and Z comprises a respiration signal, with each of the coefficients determined in response to empirical data as described above.

In some embodiments, the data may be combined with a tiered combination. While many tiered combinations can be used a tiered combination with three measurement signals can be expressed as OUTPUT=($\Delta X$)+($\Delta Y$)+($\Delta Z$)

where ($\Delta X$), ($\Delta Y$), ($\Delta Z$) may comprise change in heart rate signal from baseline, change in respiration signal from baseline and change in activity signal from baseline, and each may have a value of zero or one, based on the values of the signals. For example if the heart rate increase by 10%, ($\Delta X$) can be assigned a value of 1. If respiration increases by 5%, ($\Delta Y$) can be assigned a value of 1. If activity decreases below 10% of a baseline value ($\Delta Z$) can be assigned a value of 1. When the output signal is three, a flag may be set to trigger an alarm.

In some embodiments, the data may be combined with a logic gated combination. While many logic gated combinations can be used, a logic gated combination with three measurement signals can be expressed as OUTPUT=($\Delta X$) AND ($\Delta Y$) AND ($\Delta Z$)

where ($\Delta X$), ($\Delta Y$), ($\Delta Z$) may comprise change in heart rate signal from baseline, change in respiration signal from baseline and change in activity signal from baseline, and each may have a value of zero or one, based on the values of the signals. For example if the heart rate increase by 10%, ($\Delta X$) can be assigned a value of 1. If respiration increases by 5%, ($\Delta Y$) can be assigned a value of 1. If activity decreases below 10% of a baseline value ($\Delta Z$) can be assigned a value of 1. When each of ($\Delta X$), ($\Delta Y$), ($\Delta Z$) is one, the output signal is one, and a flag may be set to trigger an alarm. If any one of ($\Delta X$), ($\Delta Y$) or ($\Delta Z$) is zero, the output signal is zero and a flag may be set so as not to trigger an alarm. While a specific example with AND gates has been shown the data can be combined in many ways with known gates for example NAND, NOR, OR, NOT, XOR, XNOR gates. In some embodiments, the gated logic may be embodied in a truth table.

The processor system, as described above, performs the methods 500, including many of the steps described above. It should be appreciated that the specific steps illustrated in FIG. 5A provide a particular method of monitoring a patient and responding to a signal event, according to an embodiment of the present invention. Other sequences of steps may also be performed according to alternative embodiments. For example, alternative embodiments of the present invention may perform the steps outlined above in a different order. Moreover, the individual steps illustrated in FIG. 5A may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 5B:
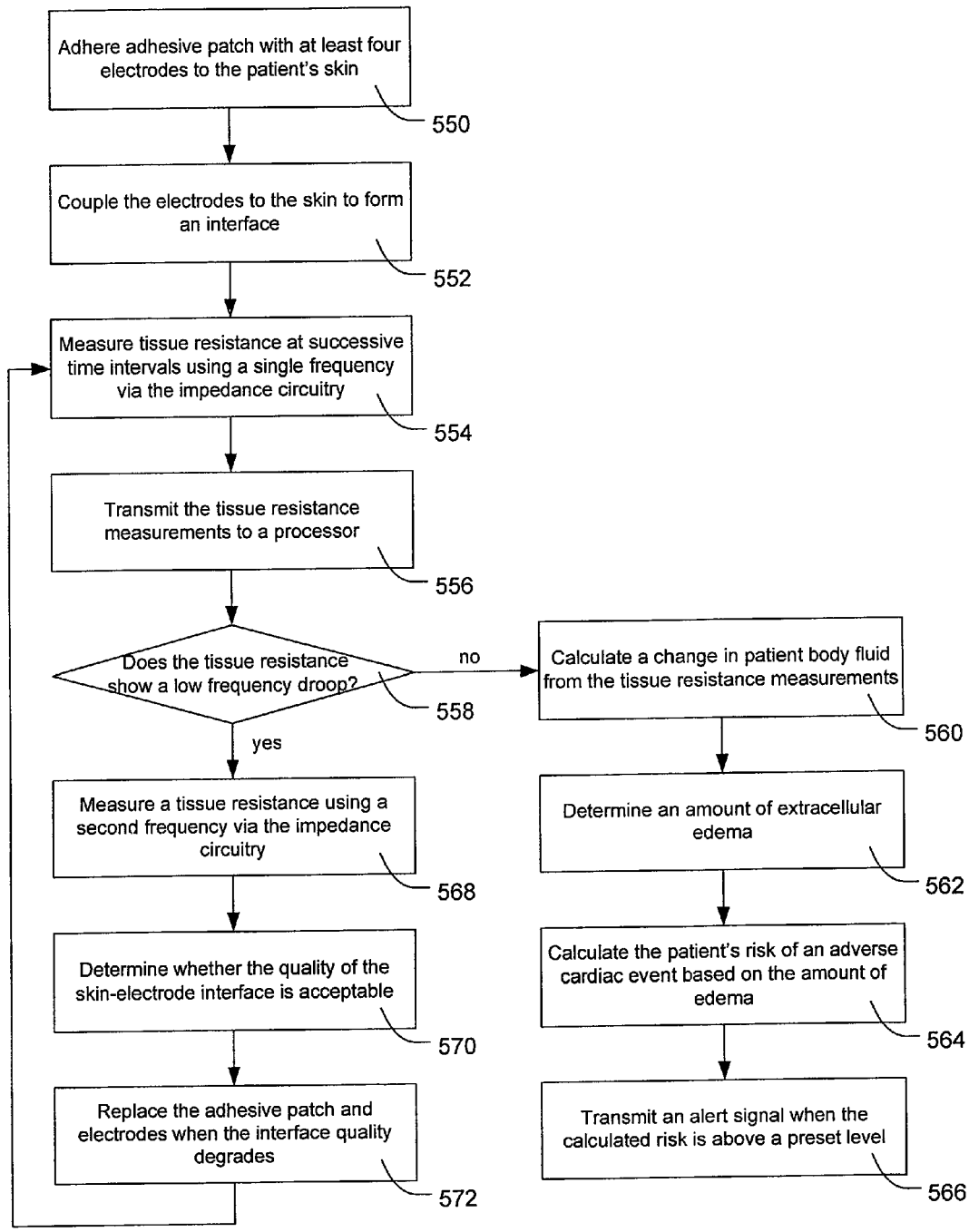
FIGS. 5B, 5C and 5D show methods for monitoring body fluid of a patient.

FIG. 5B shows a method of using bioimpedance measurements to determine changes in the body fluid of a patient for heart failure monitoring. In step 550, an adhesive patch with at least four electrodes is placed on the skin of the patient, as described above with respect to other embodiments of the invention. In step 552, the electrodes are coupled to the skin to form an interface. A single frequency is used to measure the tissue resistance via the impedance circuitry in step 554. A low frequency is preferably chosen as the single measurement frequency. There are two capacitances that must be considered when taking these measurements: the capacitance of the skin-electrode interface and the intracellular capacitance. Choosing a low frequency for the measurement frequency isolates the skin-electrode interface measurement, because at low frequencies the effect of the intracellular capacitance is negligible. The low frequency is preferably less than 200 kHz and more preferably less than 100 kHz. In a particularly preferred embodiment, the frequency is about 10 kHz. The tissue resistance measurements are transmitted to a processor in step 556.

In step 558, the processor determines whether the tissue resistance measurements exhibit a "low frequency droop." A threshold decline in the measured resistance may be selected in order to identify a low frequency droop. For example, a decline of over 10% from the nominal value of the measurements, or over 15 or 20%, may indicate an irregular or anomalous skin-electrode coupling. Wetting of the skin, such as while showering or from sweating during physical exercise, can cause a low frequency droop. To verify that an abnormal reading is caused by a wetting of the skin, a second measurement can be taken at an additional low frequency, as in step 568. The additional frequency is preferably lower than the frequency of the regular measurements. In a particularly preferred embodiment, the additional frequency is about 2 kHz. If the low frequency droop is determined to be caused by wetting of the skin, measurements can be temporarily suspended, or affected data points can be disregarded, if necessary. In step 570, the quality of the skin-electrode interface is determined, and in step 572, the adhesive patch and electrodes are replaced when necessary.

When the tissue resistance measurements do not show a low frequency droop, the processor efficiently calculates a change in the patient body fluid in step 560. As described above, the change in body fluid is related to the amount of extracellular edema, which is determined in step 562. In step 564, the amount of edema is used to calculate the patient's risk of an adverse cardiac event. An alert is transmitted in step 566 when the patient's risk exceeds a preset level.

Figure 5C:
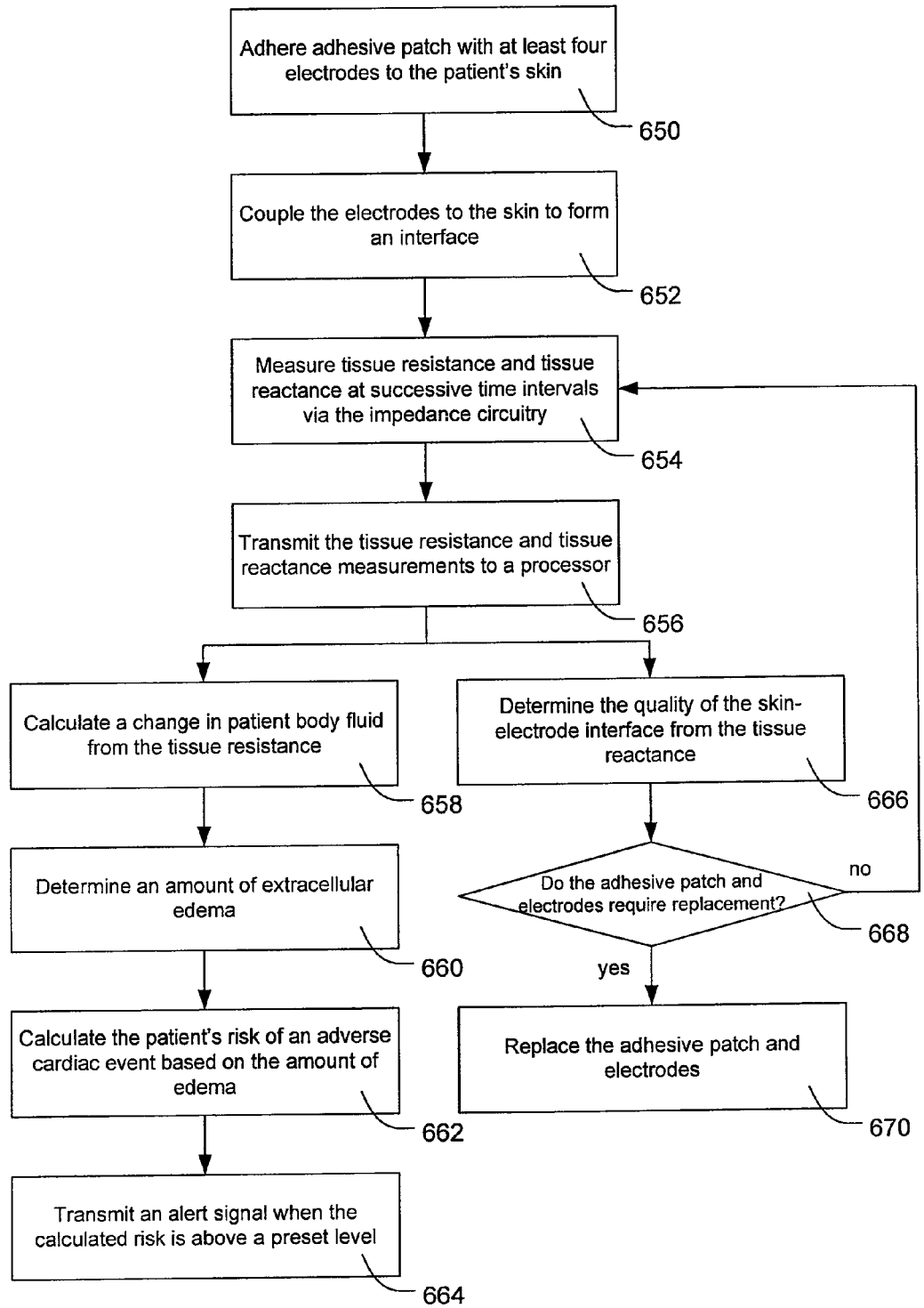

FIG. 5C shows a method of using bioimpedance measurements to determine changes in the body fluid of a patient for heart failure monitoring, where the bioimpedance measurements include tissue resistance and tissue reactance. In step 650, an adhesive patch with at least four electrodes is placed on the skin of the patient, as described above with respect to other embodiments of the invention. The electrodes are coupled to the skin to form an interface in step 652. In step 654, tissue resistance and tissue reactance are measured at successive time intervals via the impedance circuitry. The measurements are then transmitted to a processor in step 656. From the tissue resistance measurements, in step 658, the processor calculates a change in the patient body fluid. In steps 660 and 662, respectively, the amount of extracellular edema is determined and the patient's risk of an adverse cardiac event is calculated. When the risk is above a preset level, an alert signal is transmitted in step 664.

In step 666, the processor uses the tissue reactance measurements to determine the quality of the skin-electrode interface. A threshold value for the reactance may be selected such that a reactance value in excess of the threshold indicates that the quality of the skin-electrode interface is poor. For example, the reactance threshold may be set at between approximately 8 and 15 ohms, such as 10 ohms. As described above, the quality of the interface can be affected by wetting of the skin or by degradation of the adhesive strength of the adhesive patch. If the processor determines that the adhesive patch requires replacement in step 668, then it is replaced in step 670. If the adhesive patch does not require replacement, then further measurements of the tissue resistance and tissue reactance are taken.

Figure 5D:
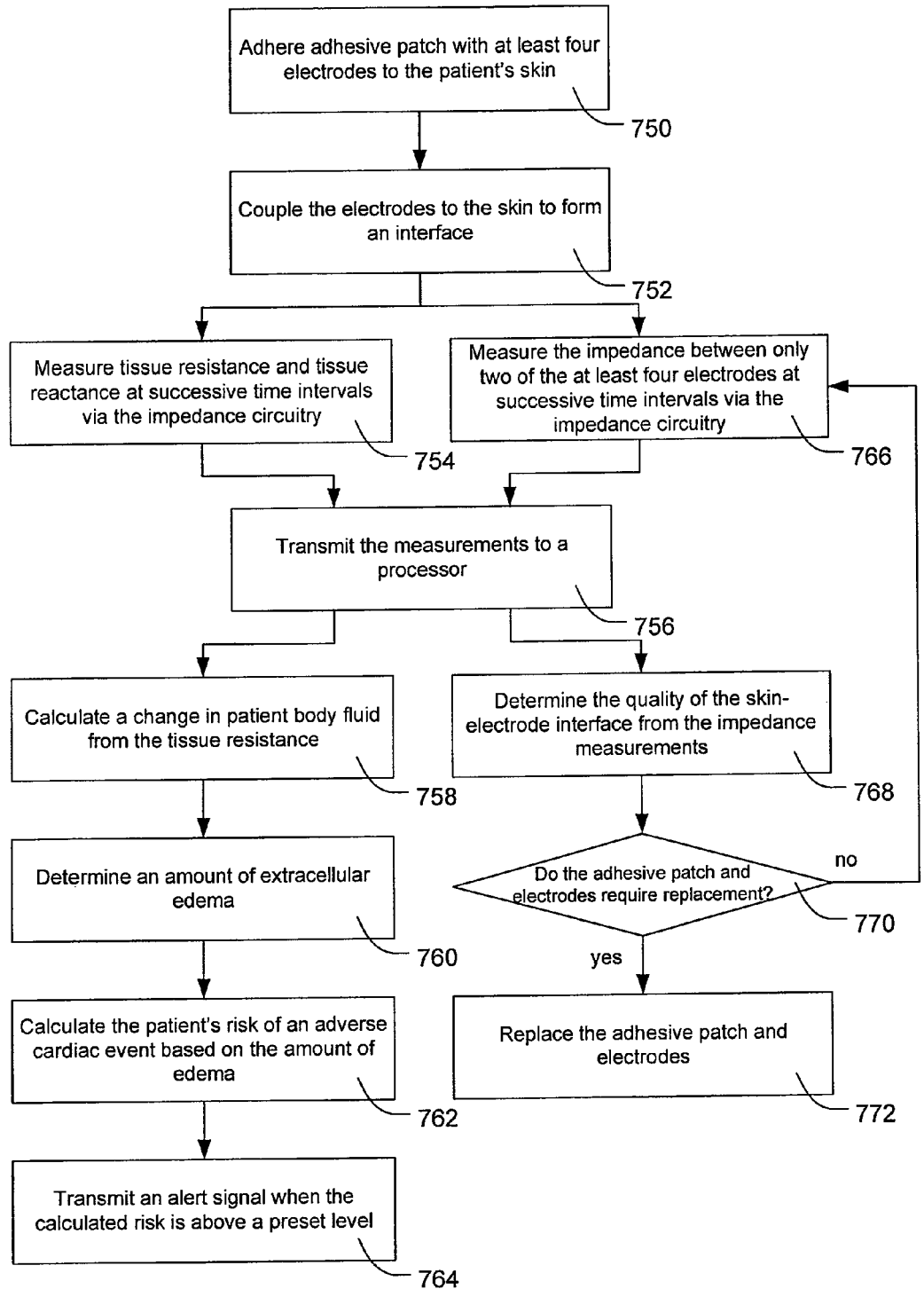

FIG. 5D shows a method of using bioimpedance measurements to determine changes in the body fluid of a patient for heart failure monitoring. The method is related to the method shown in FIG. 5C, but uses the tissue impedance measured between any two electrodes to determine the quality of the skin-electrode coupling. Steps 750 through 764 correspond to steps 650 through 664 of FIG. 5C.

In step 766, an impedance measurement is taken between any two of the electrodes coupled to the skin. The processor uses the impedance measurements to determine the quality of the skin-electrode coupling in step 768. A poor connection at the skin-electrode interface, such as when the adhesive patch begins to lose its adhesive strength, will cause the impedance measured between any two electrodes to increase. A threshold for the impedance increase may be selected, such that when the impedance measured between two electrodes exceeds the threshold, a poor skin-electrode coupling is indicated. For example, a threshold may be selected between 4 and 6 kΩ, such as 5 kΩ. If the impedance measurements indicate that the coupling is poor, then the patch and electrodes will be replaced, as in steps 770 and 772. If the patch does not require replacement, then measurements will continue to be taken.

The processor system, as described above, can perform many of the above described methods, including many of the steps described above. It should be appreciated that the specific steps illustrated above provide a particular methods of monitoring a patient, according to some embodiments of the present invention. Other sequences of steps may also be performed according to alternative embodiments. For example, alternative embodiments of the present invention may perform the steps outlined above in a different order. Moreover, the individual steps illustrated may include multiple substeps that may be performed in various sequences as appropriate to the individual step. Furthermore, additional steps may be added or removed depending on the particular applications. One of ordinary skill in the art would recognize many variations, modifications, and alternatives.

EXPERIMENTAL

FIG. 6A shows a graph of measurements of tissue resistance over a range of measurement frequencies, and FIG. 6B shows a portion of the graph of FIG. 6A enlarged. The data were measured with a patch as described above.

FIG. 6A is a graph of tissue resistance measurements taken at multiple frequencies over the range of approximately 5 to 200 kHz, where each curve represents a set of measurements taken at a different point in time. In FIG. 6B, a portion of the graph from FIG. 6A was enlarged and only four of the sets of measurements are displayed. These four sets of measurements were taken at different points in time during a single day and include one set that exhibits a low frequency droop. Comparing the measurements taken at 8:05:30 AM to the others, the graph shows that at lower frequencies, for example less than 10 kHz, the resistance may drop off severely, such as when the patch adhered to the patient is initially exposed to water, and then steadily rise back to a nominal value. The nominal value can be seen from the measurements taken at 7:42:35 AM, 10:19:05 AM and 5:39:11 PM. Here, the initial drop in measured resistance is approximately 15 ohms; however, how much the resistance measurement drops is related to the overall variability of the measurements, which is discussed below.

Electrode-to-skin coupling can affect the quality of the measurements. For example, in addition to showering, the size of the electrode can affect coupling. For example, a variation in measured resistance taken over 10 days may occur with a range of about of about 5 ohms for a patch having hydrogels 23 mm by 23 mm in size, whereas the variation in measured resistance taken over 10 days may occur with a range of about 15 ohms for a patch having hydrogels 18 mm×18 mm in size. Such a difference in variability may be due to the larger gel area providing more robust contact and coupling to the skin of the patient.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

The invention claimed is:

1. A method of monitoring a patient, the method comprising:
    adhering an adhesive patch to a skin of the patient to couple a plurality of electrodes to the skin of the patient to form a skin-electrode interface;
    measuring a plurality of tissue resistances of the patient at a first frequency with impedance circuitry coupled to the plurality of electrodes;
    detecting, with the impedance circuitry, a low frequency droop in the tissue resistance measurements made at the first frequency:
    measuring, with the impedance circuitry, a tissue resistance of the patient at a second frequency, wherein the second frequency is lower than the first frequency;
    verifying, with the impedance circuitry, the detection of low frequency droop based on the tissue resistance measured at the second frequency; and
    temporarily suspending data collection with the impedance circuitry based at least in part on the fact that the low frequency droop has been detected and verified.

2. The method of claim 1, wherein the first frequency is less than 100 kHz.

3. The method of claim 1, wherein the first frequency is less than 20 kHz.

4. The method of claim 1, wherein the second frequency is equal to about 2 kHz.

5. The method of claim 1, wherein low frequency droop is detected when the measured tissue resistances at the first frequency declines by a threshold amount.

6. The method of claim 5, wherein the threshold amount is a decline of more than 10%.

7. The method of claim 5, wherein the threshold amount is a decline of more than 20%.

8. The method of claim 1, further including calculating a change in patient body fluid based on the tissue resistance measured at the first frequency if no low frequency droop is detected.

9. An adherent device to monitor a tissue hydration of a patient, the device comprising:
    an adhesive patch to adhere to a skin of the patient;
    a plurality of electrodes connected to the patch and capable of electrically coupling to the patient; and
    circuitry coupled to the plurality of electrodes to measure a plurality of tissue resistances of the patient at a first frequency and to detect a low frequency droop in the measured tissue resistances, wherein in response to detected low frequency droop, the circuitry is configured to measure a tissue resistance of the patient at a second frequency that is lower than the first frequency to verify the detection of low frequency droop, and to temporarily suspend data collection based on the detection and verification of low frequency droop.

10. The adherent device of claim 9, wherein the first frequency is less than 100 kHz.

11. The adherent device of claim 9, wherein the first frequency is less than 20 kHz.

12. The adherent device of claim 9, wherein the second frequency is equal to about 2 kHz.

13. The adherent device of claim 9, wherein the circuitry is configured to detect low frequency droop when the measured tissue resistances at the first frequency declines by a threshold amount.

14. The adherent device of claim 13, wherein the threshold amount is a decline of more than 10%.

15. The adherent device of claim 13, wherein the threshold amount is a decline of more than 20%.

16. The adherent deice of claim 9, wherein the circuitry is further configured to calculate a change in patient body fluid based on the tissue resistance measured at the first frequency if no low frequency droop is detected.

\* \* \* \* \*